United States Patent
Shen et al.

(10) Patent No.: US 12,134,644 B2
(45) Date of Patent: Nov. 5, 2024

(54) ANTI-IL-17A ANTIBODIES AND USE THEREOF

(71) Applicants: Weiqun Shen, Napa, CA (US); Xiangyang Tan, Tewksbury, MA (US); Jianning Liu, Suzhou (CN)

(72) Inventors: Weiqun Shen, Napa, CA (US); Xiangyang Tan, Tewksbury, MA (US); Jianning Liu, Suzhou (CN)

( * ) Notice: Subject to any disclaimer, the term of this patent is extended or adjusted under 35 U.S.C. 154(b) by 950 days.

(21) Appl. No.: 17/264,700

(22) PCT Filed: Jul. 30, 2019

(86) PCT No.: PCT/CN2019/098327
§ 371 (c)(1),
(2) Date: Jan. 29, 2021

(87) PCT Pub. No.: WO2020/024931
PCT Pub. Date: Feb. 6, 2020

(65) Prior Publication Data
US 2021/0309735 A1 Oct. 7, 2021

(30) Foreign Application Priority Data
Jul. 31, 2018 (WO) ................ PCT/CN2018/097795

(51) Int. Cl.
*C07K 16/24* (2006.01)
*A61K 39/00* (2006.01)
*A61P 19/02* (2006.01)

(52) U.S. Cl.
CPC ............ *C07K 16/244* (2013.01); *A61P 19/02* (2018.01); *A61K 2039/505* (2013.01); *C07K 2317/24* (2013.01); *C07K 2317/76* (2013.01); *C07K 2317/92* (2013.01)

(58) Field of Classification Search
None
See application file for complete search history.

(56) References Cited

U.S. PATENT DOCUMENTS

2017/0355756 A1* 12/2017 Julien .................... C07K 16/18

FOREIGN PATENT DOCUMENTS

| CN | 101001645 A | 7/2007 | |
| CN | 103936854 A | 7/2014 | |
| CN | 104231080 A | 12/2014 | |
| CN | 107522783 A | 12/2017 | |
| WO | WO-2008068048 A2 * | 6/2008 | ............ A61P 31/10 |
| WO | 2009082624 A2 | 7/2009 | |

OTHER PUBLICATIONS

Kuwabara T, Ishikawa F, Kondo M, Kakiuchi T. The Role of IL-17 and Related Cytokines in Inflammatory Autoimmune Diseases. Mediators Inflamm. 2017;2017:3908061. (Year: 2017).*
Almagro JC, Fransson J. Humanization of antibodies. Front Biosci. Jan. 1, 2008;13:1619-33. (Year: 2008).*
Chen et al., Enhancement and destruction of antibody function by somatic mutation: unequal occurrence is controlled by V gene combinatorial associations. EMBO J. Jun. 15, 1995;14(12):2784-94. (Year: 1995).*
Koenig et al. Mutational landscape of antibody variable domains reveals a switch modulating the interdomain conformational dynamics and antigen binding. PNAS Jan. 24, 2017 114(4)E486-E495;firstpublished Jan. 5, 2017. (Year: 2017).*
Kussie et al. A single engineered amino acid substitution changes antibody fine specificity.J Immunol. Jan. 1, 1994;152(1):146-52. (Year: 1994).*
Langley RG et al. Secukinumab in plaque psoriasis—results of two phase 3 trials. N Engl J Med. Jul. 24, 2014;371(4):326-38. (Year: 2014).*
Kolbinger F et al. Secukinumab for the treatment of psoriasis, psoriatic arthritis, and axial spondyloarthritis: Physical and pharmacological properties underlie the observed clinical efficacy and safety. Pharmacol Ther. Jan. 2022;229:107925. (Year: 2022).*
Liu, L. et al. "Generation and characterization of ixekizumab, a humanized monoclonal antibody that neutralizes interleukin-17A", Journal of Inflammation Research, vol. 9, Apr. 19, 2016 (Apr. 19, 2016), pp. 41-48.
Kurschus, F.C. et al. "IL-17 for therapy", Journal of Dermatological Science, vol. 87, Dec. 31, 2017 (Dec. 31, 2017), pp. 221-227.
International Search Report, Application No. PCT/CN2019/098327 mailed Nov. 1, 2019. ISA/National Intellectual Property Administration, Beijing, CN.

* cited by examiner

*Primary Examiner* — Aurora M Fontainhas
*Assistant Examiner* — Jennifer A Benavides
(74) *Attorney, Agent, or Firm* — Honigman LLP; Thomas A. Wootton, Esq.; Jonathan P. O'Brien

(57) ABSTRACT

The present disclosure provides an antibody, or an antigen binding fragment thereof, which specifically binds to IL-17A with high affinity. The present disclosure also provides a method for preparing and using said antibody.

14 Claims, 6 Drawing Sheets
Specification includes a Sequence Listing.

FIG.1

```
                             SEQUENCE LISTING

<160> NUMBER OF SEQ ID NOS: 30

<210> SEQ ID NO 1
   <211> LENGTH: 8
   <212> TYPE: PRT
   <213> ORGANISM: Artificial Sequence
   <220> FEATURE:
   <223> OTHER INFORMATION: HCDR1

<400> SEQUENCE: 1

Gly Phe Thr Phe Ser Thr Tyr Gly
   1               5

<210> SEQ ID NO 2
   <211> LENGTH: 8
   <212> TYPE: PRT
   <213> ORGANISM: Artificial Sequence
   <220> FEATURE:
   <223> OTHER INFORMATION: HCDR2

<400> SEQUENCE: 2

Ile Asn His Asn Gly Gly Ser Thr
   1               5

<210> SEQ ID NO 3
   <211> LENGTH: 13
   <212> TYPE: PRT
   <213> ORGANISM: Artificial Sequence
   <220> FEATURE:
   <223> OTHER INFORMATION: HCDR3

<400> SEQUENCE: 3

Ala Arg Asp Pro Arg His Asp Gly Tyr Phe Phe Asp Tyr
   1               5                   10

<210> SEQ ID NO 4
   <211> LENGTH: 6
   <212> TYPE: PRT
   <213> ORGANISM: Artificial Sequence
   <220> FEATURE:
   <223> OTHER INFORMATION: LCDR1

<400> SEQUENCE: 4

Glu Asp Ile Tyr Asp Arg
   1               5

<210> SEQ ID NO 5
   <211> LENGTH: 3
   <212> TYPE: PRT
   <213> ORGANISM: Artificial Sequence
   <220> FEATURE:
```

<223> OTHER INFORMATION: LCDR2

<400> SEQUENCE: 5

Gly Ala Thr
1

<210> SEQ ID NO 6
<211> LENGTH: 9
<212> TYPE: PRT
<213> ORGANISM: Artificial Sequence
<220> FEATURE:
<223> OTHER INFORMATION: LCDR3

<400> SEQUENCE: 6

Gln Gln Tyr Trp Ser Val Pro Trp Thr
1               5

<210> SEQ ID NO 7
<211> LENGTH: 120
<212> TYPE: PRT
<213> ORGANISM: Mus musculus

<400> SEQUENCE: 7

Glu Val Gln Leu Val Glu Ser Gly Gly Gly Leu Val Gln Pro Gly Gly
1               5                   10                  15

Ser Leu Lys Leu Ser Cys Val Ala Ser Gly Phe Thr Phe Ser Thr Tyr
            20                  25                  30

Gly Met Ser Trp Val Arg Gln Thr Pro Asp Lys Arg Leu Glu Leu Val
        35                  40                  45

Ala Ile Ile Asn His Asn Gly Ser Thr Phe Tyr Pro Asp Ser Val
    50                  55                  60

Lys Gly Arg Phe Thr Val Ser Arg Asp Asn Ala Lys Asn Thr Leu His
65                  70                  75                  80

Leu Gln Met Ser Ser Leu Lys Ser Glu Asp Thr Ala Met Tyr Tyr Cys
                85                  90                  95

Ala Arg Asp Pro Arg His Asp Gly Tyr Phe Phe Asp Tyr Trp Gly Gln
            100                 105                 110

Gly Thr Thr Leu Thr Val Ser Ser
        115                 120

<210> SEQ ID NO 8
<211> LENGTH: 107
<212> TYPE: PRT
<213> ORGANISM: Mus musculus

<400> SEQUENCE: 8

Asp Ile Gln Met Thr Gln Ser Ser Pro Ser Phe Ser Val Ser Leu Gly
1               5                   10                  15

Asp Arg Val Thr Ile Thr Cys Lys Ala Ser Glu Asp Ile Tyr Asp Arg
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Ile Pro Ser Arg Phe Ser Gly
    50                  55                  60

Ser Arg Ser Gly Lys Asp Tyr Thr Leu Asp Ile Asn Ser Leu Gln Thr
65                  70                  75                  80

Glu Asp Ala Ala Thr Tyr Tyr Cys Gln Gln Tyr Trp Ser Val Pro Trp
                85                  90                  95

Thr Phe Gly Gly Gly Thr Lys Leu Glu Ile Lys

<210> SEQ ID NO 9
<211> LENGTH: 470
<212> TYPE: PRT
<213> ORGANISM: Mus musculus

<400> SEQUENCE: 9

```
Met Asp Pro Lys Gly Ser Leu Ser Trp Arg Ile Leu Leu Phe Leu Ser
1               5                   10                  15

Leu Ala Phe Glu Leu Ser Tyr Gly Glu Val Gln Leu Val Glu Ser Gly
                20                  25                  30

Gly Gly Leu Val Gln Pro Gly Gly Ser Leu Lys Leu Ser Cys Val Ala
            35                  40                  45

Ser Gly Phe Thr Phe Ser Thr Tyr Gly Met Ser Trp Val Arg Gln Thr
        50                  55                  60

Pro Asp Lys Arg Leu Glu Leu Val Ala Ile Ile Asn His Asn Gly Gly
65                  70                  75                  80

Ser Thr Phe Tyr Pro Asp Ser Val Lys Gly Arg Phe Thr Val Ser Arg
                85                  90                  95

Asp Asn Ala Lys Asn Thr Leu His Leu Gln Met Ser Ser Leu Lys Ser
                100                 105                 110

Glu Asp Thr Ala Met Tyr Tyr Cys Ala Arg Asp Pro Arg His Asp Gly
            115                 120                 125

Tyr Phe Phe Asp Tyr Trp Gly Gln Gly Thr Thr Leu Thr Val Ser Ser
        130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
                180                 185                 190

Gly Val His Thr Phe Pro Ala Val Leu Gln Ser Ser Gly Leu Tyr Ser
            195                 200                 205

Leu Ser Ser Val Val Thr Val Pro Ser Ser Leu Gly Thr Lys Thr
        210                 215                 220

Tyr Thr Cys Asn Val Asp His Lys Pro Ser Asn Thr Lys Val Asp Lys
225                 230                 235                 240

Arg Val Glu Ser Lys Tyr Gly Pro Pro Cys Pro Pro Cys Pro Ala Pro
                245                 250                 255

Glu Phe Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser Gln Glu Asp Pro Glu Val Gln Phe Asn Trp Tyr Val Asp
        290                 295                 300

Gly Val Glu Val His Asn Ala Lys Thr Lys Pro Arg Glu Glu Gln Phe
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Gly Leu
            340                 345                 350

Pro Ser Ser Ile Glu Lys Thr Ile Ser Lys Ala Lys Gly Gln Pro Arg
        355                 360                 365
```

```
Glu Pro Gln Val Tyr Thr Leu Pro Pro Ser Gln Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Arg Leu Thr Val Asp Lys Ser Arg Trp Gln Gly Asn Val Phe Ser
        435                 440                 445

Cys Ser Val Met His Glu Ala Leu His Asn His Tyr Thr Gln Lys Ser
450                 455                 460

Leu Ser Leu Ser Leu Gly
465                 470

<210> SEQ ID NO 10
<211> LENGTH: 234
<212> TYPE: PRT
<213> ORGANISM: Mus musculus

<400> SEQUENCE: 10

Met Glu Thr Asp Thr Leu Leu Leu Trp Val Leu Leu Leu Trp Val Pro
1               5                   10                  15

Gly Ser Thr Gly Asp Ile Gln Met Thr Gln Ser Ser Pro Ser Phe Ser
            20                  25                  30

Val Ser Leu Gly Asp Arg Val Thr Ile Thr Cys Lys Ala Ser Glu Asp
        35                  40                  45

Ile Tyr Asp Arg Leu Ala Trp Tyr Gln Gln Lys Pro Gly Asn Ala Pro
    50                  55                  60

Arg Leu Leu Ile Ser Gly Ala Thr Ser Leu Glu Thr Gly Ile Pro Ser
65                  70                  75                  80

Arg Phe Ser Gly Ser Arg Ser Gly Lys Asp Tyr Thr Leu Asp Ile Asn
                85                  90                  95

Ser Leu Gln Thr Glu Asp Ala Ala Thr Tyr Tyr Cys Gln Gln Tyr Trp
            100                 105                 110

Ser Val Pro Trp Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 11
<211> LENGTH: 470
<212> TYPE: PRT
<213> ORGANISM: Artificial Sequence
```

```
<220> FEATURE:
<223> OTHER INFORMATION: heavy chain 6665; PP10760 H; PP10761 H; PP10762
      H

<400> SEQUENCE: 11

Met Asp Pro Lys Gly Ser Leu Ser Trp Arg Ile Leu Leu Phe Leu Ser
1               5                   10                  15

Leu Ala Phe Glu Leu Ser Tyr Gly Glu Val Gln Leu Val Glu Ser Gly
            20                  25                  30

Gly Gly Leu Val Gln Pro Gly Gly Ser Leu Arg Leu Ser Cys Ala Ala
        35                  40                  45

Ser Gly Phe Thr Phe Ser Thr Tyr Gly Met Ser Trp Val Arg Gln Ala
50                  55                  60

Pro Gly Lys Gly Leu Glu Leu Val Ser Ile Ile Asn His Asn Gly Gly
65                  70                  75                  80

Ser Thr Phe Tyr Pro Asp Ser Val Lys Gly Arg Phe Thr Ile Ser Arg
                85                  90                  95

Asp Asn Ser Lys Asn Thr Leu Tyr Leu Gln Met Asn Ser Leu Arg Ala
            100                 105                 110

Glu Asp Thr Ala Val Tyr Tyr Cys Ala Arg Asp Pro Arg His Asp Gly
        115                 120                 125

Tyr Phe Phe Asp Tyr Trp Gly Gln Gly Thr Leu Val Thr Val Ser Ser
130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Lys Thr
210                 215                 220

Tyr Thr Cys Asn Val Asp His Lys Pro Ser Asn Thr Lys Val Asp Lys
225                 230                 235                 240

Arg Val Glu Ser Lys Tyr Gly Pro Pro Cys Pro Pro Cys Pro Ala Pro
                245                 250                 255

Glu Phe Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser Gln Glu Asp Pro Glu Val Gln Phe Asn Trp Tyr Val Asp
290                 295                 300

Gly Val Glu Val His Asn Ala Lys Thr Lys Pro Arg Glu Glu Gln Phe
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Gly Leu
            340                 345                 350

Pro Ser Ser Ile Glu Lys Thr Ile Ser Lys Ala Lys Gly Gln Pro Arg
        355                 360                 365

Glu Pro Gln Val Tyr Thr Leu Pro Pro Ser Gln Glu Glu Met Thr Lys
370                 375                 380

Asn Gln Val Ser Leu Thr Cys Leu Val Lys Gly Phe Tyr Pro Ser Asp
```

```
            385                 390                 395                 400
Ile Ala Val Glu Trp Glu Ser Asn Gly Gln Pro Glu Asn Asn Tyr Lys
                    405                 410                 415

Thr Thr Pro Pro Val Leu Asp Ser Asp Gly Ser Phe Phe Leu Tyr Ser
                420                 425                 430

Arg Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
        450                 455                 460

Leu Ser Leu Ser Leu Gly
465                 470

<210> SEQ ID NO 12
<211> LENGTH: 120
<212> TYPE: PRT
<213> ORGANISM: Artificial Sequence
<220> FEATURE:
<223> OTHER INFORMATION: VH6665; PP10760 VH; PP10761 VH; PP10762 VH

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
                20                  25                  30

Gly Met Ser Trp Val Arg Gln Ala Pro Gly Lys Gly Leu Glu Leu Val
            35                  40                  45

Ser Ile Ile Asn His Asn Gly Gly Ser Thr Phe Tyr Pro Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Arg His Asp Gly Tyr Phe Phe Asp Tyr Trp Gly Gln
            100                 105                 110

Gly Thr Leu Val Thr Val Ser Ser
        115                 120

<210> SEQ ID NO 13
<211> LENGTH: 1416
<212> TYPE: DNA
<213> ORGANISM: Artificial Sequence
<220> FEATURE:
<223> OTHER INFORMATION: heavy chain 6665 nucleotide; PP10760 H
      nucleotide; PP10761 H nucleotide; PP10762 H nucleotide

<400> SEQUENCE: 13
atggacccca agggcagcct gagctggaga atcctgctgt cctgagccct ggccttcgag      60
ctgagctacg gcgaggtgca actggtggag tccggcggag gtctggtgca gcccggtggc     120
agcctgaggc tgtcatgcgc agccagcggc ttcaccttca gcacctacgg catgagctgg     180
gtgaggcagg cacccggcaa gggcctggag ctggtgagca tcatcaacca caacggcggc     240
agtacctttt accccgacag cgtgaagggc aggttcacca tcagcaggga caacagcaag     300
aacaccctgt acctgcagat gaactcactg agggcagagg acaccgccgt gtactactgc     360
gccagggacc ccaggcatga cgggtacttc ttcgactact ggggccaggg caccctggtg     420
acagttagct ctgctagcac caagggcccc agcgtgtttc ctctcgctcc ctgcagccgg     480
agcacatccg agagcaccgc tgctctgggc tgtctcgtga aggactactt ccctgaaccc     540
```

```
gtcaccgtca gctggaatag cggcgccctg acatccggcg tccacacatt ccccgctgtc    600
ctgcagagca gcggcctgta cagcctgagc tccgtggtca ccgtgcctag cagcagcctg    660
ggaacaaaga cctacacctg caacgtggac cataagccct ccaacaccaa ggtggacaag    720
cgggtggaat ccaagtatgg accccccgt cctccttgcc ctgctcctga atttctcgga    780 ggccccctccg tcttcctgtt tccccccaag cccaaggaca ccctgatgat ctcccggaca    840
cccgaagtca cctgcgtcgt ggtggatgtc agccaggaag atcccgaggt gcagttcaac    900
tggtacgtgg acggagtgga ggtgcataac gccaaaacca gcccaggga gagcagttc    960 aacagcacct atcgggtcgt gtccgtgctc accgtcctgc atcaggattg gctcaacggc   1020
aaggagtaca agtgcaaggt gtccaacaag ggcctgccct cctccatcga aagaccatc   1080 tccaaggcta agggccaacc tcgggagccc aagtgtata ccctccctcc agccaggag   1140 gagatgacca agaatcaagt gagcctgacc tgcctcgtga agggatttta ccctccgac   1200 atcgctgtgg aatgggaaag caatggccaa cctgagaaca actacaagac cacacccccc   1260
gtgctggact ccgatggctc cttcttcctg tacagcaggc tgaccgtgga caaatcccgg   1320
tggcaagagg gaaacgtgtt cagctgctcc gtgatgcacg aggctctcca caaccactac   1380
acccagaaga gcctctccct gagcctcggc tagtaa                              1416
```

<210> SEQ ID NO 14
<211> LENGTH: 470
<212> TYPE: PRT
<213> ORGANISM: Artificial Sequence
<220> FEATURE:
<223> OTHER INFORMATION: heavy chain 6666; PP10763 H; PP10764 H; PP10765 H

<400> SEQUENCE: 14

```
Met Asp Pro Lys Gly Ser Leu Ser Trp Arg Ile Leu Leu Phe Leu Ser
1               5                   10                  15

Leu Ala Phe Glu Leu Ser Tyr Gly Glu Val Gln Leu Val Glu Ser Gly
            20                  25                  30

Gly Gly Leu Val Gln Pro Gly Gly Ser Leu Arg Leu Ser Cys Ala Ala
        35                  40                  45

Ser Gly Phe Thr Phe Ser Thr Tyr Gly Met Ser Trp Val Arg Gln Ala
    50                  55                  60

Pro Gly Lys Gly Leu Glu Leu Val Ala Ile Ile Asn His Asn Gly Gly
65                  70                  75                  80

Ser Thr Phe Tyr Pro Asp Ser Val Lys Gly Arg Phe Thr Val Ser Arg
                85                  90                  95

Asp Asn Ser Lys Asn Thr Leu Tyr Leu Gln Met Asn Ser Leu Arg Ala
            100                 105                 110

Glu Asp Thr Ala Val Tyr Tyr Cys Ala Arg Asp Pro Arg His Asp Gly
        115                 120                 125

Tyr Phe Phe Asp Tyr Trp Gly Gln Gly Thr Leu Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
```

|         |         |         |         |         | 195     |         |         |         |         | 200     |         |         |         |         | 205     |         |         |         |
|---------|---------|---------|---------|---------|---------|---------|---------|---------|---------|---------|---------|---------|---------|---------|---------|---------|---------|---------|

Leu Ser Ser Val Val Thr Val Pro Ser Ser Leu Gly Thr Lys Thr
210                 215                 220

Tyr Thr Cys Asn Val Asp His Lys Pro Ser Asn Thr Lys Val Asp Lys
225                 230                 235                 240

Arg Val Glu Ser Lys Tyr Gly Pro Pro Cys Pro Pro Cys Pro Ala Pro
                245                 250                 255

Glu Phe Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser Gln Glu Asp Pro Glu Val Gln Phe Asn Trp Tyr Val Asp
    290                 295                 300

Gly Val Glu Val His Asn Ala Lys Thr Lys Pro Arg Glu Glu Gln Phe
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Gly Leu
            340                 345                 350

Pro Ser Ser Ile Glu Lys Thr Ile Ser Lys Ala Lys Gly Gln Pro Arg
        355                 360                 365

Glu Pro Gln Val Tyr Thr Leu Pro Pro Ser Gln Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Arg Leu Thr Val Asp Lys Ser Arg Trp Gln Glu Gly Asn Val Phe Ser
        435                 440                 445

Cys Ser Val Met His Glu Ala Leu His Asn His Tyr Thr Gln Lys Ser
    450                 455                 460

Leu Ser Leu Ser Leu Gly
465                 470

```
<210> SEQ ID NO 15
<211> LENGTH: 120
<212> TYPE: PRT
<213> ORGANISM: Artificial Sequence
<220> FEATURE:
<223> OTHER INFORMATION: VH6666; PP10763 VH; PP10764 VH; PP10765 VH

<400> SEQUENCE: 15
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met Ser Trp Val Arg Gln Ala Pro Gly Lys Gly Leu Glu Leu Val
        35                  40                  45

Ala Ile Ile Asn His Asn Gly Gly Ser Thr Phe Tyr Pro Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                    85                  90                  95
Ala Arg Asp Pro Arg His Asp Gly Tyr Phe Phe Asp Tyr Trp Gly Gln
                100                 105                 110

Gly Thr Leu Val Thr Val Ser Ser
        115                 120

<210> SEQ ID NO 16
<211> LENGTH: 1416
<212> TYPE: DNA
<213> ORGANISM: Artificial Sequence
<220> FEATURE:
<223> OTHER INFORMATION: heavy chain 6666 nucleotide; PP10763 H
      nucleotide; PP10764 H nucleotide; PP10765 H nucleotide

<400> SEQUENCE: 16
atggacccca agggcagcct gagctggaga atcctgctgt tcctgagcct ggccttcgag      60
ctgagctacg gcgaggtgca actggtggag tccggcggag gtctggtgca gcccggtggc     120
agcctgaggc tgtcatgcgc agccagcggc ttcaccttca gcacctacgg catgagctgg     180
gtgaggcagg caccggcaa gggcctggag ctggtggcaa tcatcaacca acggcggc       240 agtacctttt accccgacag cgtgaagggc aggttcaccg tcagcaggga acagcaag       300 aacacccctgt acctgcagat gaactcactg agggcagagg acaccgccgt gtactactgc    360
gccagggacc ccaggcatga cgggtacttc ttcgactact ggggccaggg caccctggtg    420
acagttagct ctgctagcac caagggcccc agcgtgtttc ctctcgctcc ctgcagccgg    480
agcacatccg agagcaccgc tgctctgggc tgtctcgtga aggactactt ccctgaaccc    540
gtcaccgtca gctggaatag cggcgccctg acatccggcg tccacacatt ccccgctgtc    600
ctgcagagca gcggcctgta cagcctgagc tccgtggtca ccgtgcctag cagcagcctg    660
ggaacaaaga cctacacctg caacgtggac cataagccct ccaacaccaa ggtggacaag    720
cgggtggaat ccaagtatgg accccccgt cctccttgcc ctgctcctga atttctcgga    780 ggccccctccg tcttcctgtt tccccccaag cccaaggaca cctgatgat ctcccggaca    840 cccgaagtca cctgcgtcgt ggtggatgtc agcaggaag atccgaggt gcagttcaac    900 tggtacgtgg acggagtgga ggtgcataac gccaaaacca gcccaggga gagcagttc    960 aacagcacct atcgggtcgt gtccgtgctc accgtcctgc atcaggattg gctcaacggc   1020
aaggagtaca agtgcaaggt gtccaacaag ggcctgccct cctccatcga aagaccatc   1080 tccaaggcta agggccaacc tcgggagccc caagtgtata ccctcctctcc cagccaggag   1140 gagatgacca gaatcaagt gagcctgacc tgcctcgtga agggatttta ccctccgac    1200 atcgctgtgg aatgggaaag caatggccaa cctgagaaca actacaagac cacaccccc    1260 gtgctggact ccgatggctc cttcttcctg tacagcaggc tgaccgtgga caatccccgg   1320
tggcaagagg gaaacgtgtt cagctgctcc gtgatgcacg aggctctcca caaccactac   1380
acccagaaga gcctctcccct gagcctcggc tagtaa                                  1416

<210> SEQ ID NO 17
<211> LENGTH: 470
<212> TYPE: PRT
<213> ORGANISM: Artificial Sequence
<220> FEATURE:
<223> OTHER INFORMATION: heavy chain 6667; PP10766 H; PP10767 H; PP10768
      H

<400> SEQUENCE: 17

Met Asp Pro Lys Gly Ser Leu Ser Trp Arg Ile Leu Leu Phe Leu Ser
```

-continued

```
  1               5                   10                  15
Leu Ala Phe Glu Leu Ser Tyr Gly Glu Val Gln Leu Val Glu Ser Gly
                 20                  25                  30

Gly Gly Val Val Gln Pro Gly Arg Ser Leu Arg Leu Ser Cys Ala Ala
             35                  40                  45

Ser Gly Phe Thr Phe Ser Thr Tyr Gly Met Ser Trp Val Arg Gln Ala
         50                  55                  60

Pro Gly Lys Gly Leu Glu Leu Val Ala Ile Ile Asn His Asn Gly Gly
 65                  70                  75                  80

Ser Thr Phe Tyr Pro Asp Ser Val Lys Gly Arg Phe Thr Ile Ser Arg
                 85                  90                  95

Asp Asn Ser Lys Asn Thr Leu Tyr Leu Gln Met Asn Ser Leu Arg Ala
                100                 105                 110

Glu Asp Thr Ala Val Tyr Tyr Cys Ala Arg Asp Pro Arg His Asp Gly
            115                 120                 125

Tyr Phe Phe Asp Tyr Trp Gly Gln Gly Thr Leu Val Thr Val Ser Ser
130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Lys Thr
210                 215                 220

Tyr Thr Cys Asn Val Asp His Lys Pro Ser Asn Thr Lys Val Asp Lys
225                 230                 235                 240

Arg Val Glu Ser Lys Tyr Gly Pro Pro Cys Pro Pro Cys Pro Ala Pro
                245                 250                 255

Glu Phe Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser Gln Glu Asp Pro Glu Val Gln Phe Asn Trp Tyr Val Asp
    290                 295                 300

Gly Val Glu Val His Asn Ala Lys Thr Lys Pro Arg Glu Glu Gln Phe
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Gly Leu
            340                 345                 350

Pro Ser Ser Ile Glu Lys Thr Ile Ser Lys Ala Lys Gly Gln Pro Arg
        355                 360                 365

Glu Pro Gln Val Tyr Thr Leu Pro Pro Ser Gln Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430
```

Arg Leu Thr Val Asp Lys Ser Arg Trp Gln Glu Gly Asn Val Phe Ser
            435                 440                 445

Cys Ser Val Met His Glu Ala Leu His Asn His Tyr Thr Gln Lys Ser
    450                 455                 460

Leu Ser Leu Ser Leu Gly
465             470

<210> SEQ ID NO 18
<211> LENGTH: 120
<212> TYPE: PRT
<213> ORGANISM: Artificial Sequence
<220> FEATURE:
<223> OTHER INFORMATION: VH6667; PP10766 VH; PP10767 VH; PP10768 VH

<400> SEQUENCE: 18

Glu Val Gln Leu Val Glu Ser Gly Gly Gly Val Gln Pro Gly Arg
1               5                   10                  15

Ser Leu Arg Leu Ser Cys Ala Ala Ser Gly Phe Thr Phe Ser Thr Tyr
            20                  25                  30

Gly Met Ser Trp Val Arg Gln Ala Pro Gly Lys Gly Leu Glu Leu Val
        35                  40                  45

Ala Ile Ile Asn His Asn Gly Gly Ser Thr Phe Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Arg His Asp Gly Tyr Phe Phe Asp Tyr Trp Gly Gln
            100                 105                 110

Gly Thr Leu Val Thr Val Ser Ser
        115                 120

<210> SEQ ID NO 19
<211> LENGTH: 1416
<212> TYPE: DNA
<213> ORGANISM: Artificial Sequence
<220> FEATURE:
<223> OTHER INFORMATION: heavy chain 6667 nucleotide; PP10766 H
      nucleotide; PP10767 H nucleotide; PP10768 H nucleotide

<400> SEQUENCE: 19
atggacccca agggcagcct gagctggaga atcctgctgt tcctgagcct ggccttcgag      60
ctgagctacg cgaggtgca actggtggag tccggcggag gtgtggtgca gcccggtcgc     120
agcctgaggc tgtcatgcgc agccagcggc ttcaccttca gcacctacgg catgagctgg     180
gtgaggcagg cacccggcaa gggctggag ctggtggcaa tcatcaacca caacggcggc     240
agtacctttt accccgacag cgtgaagggc aggttcacca tcagcaggga caacagcaag     300
aacaccctgt acctgcagat gaactcactg agggcagagg acaccgccgt gtactactgc     360
gccagggacc ccaggcatga cgggtacttc ttcgactact ggggccaggg caccctggtg     420
acagttagct ctgctagcac caaggggccc agcgtgtttc ctctcgctcc ctgcagccgg     480
agcacatccg agagcaccgc tgctctgggc tgtctcgtga aggactactt ccctgaaccc     540
gtcaccgtca gctggaatag cggcgccctg acatccggcg tccacacatt ccccgctgtc     600
ctgcagagca gcggcctgta cagcctgagc tccgtggtca ccgtgcctag cagcagcctg     660
ggaacaaaga cctacacctg caacgtggac cataagccct ccaacaccaa ggtggacaag     720

```
cgggtggaat ccaagtatgg acccccctgt cctccttgcc ctgctcctga atttctcgga    780
ggcccctccg tcttcctgtt tcccccccaag cccaaggaca ccctgatgat ctcccggaca    840
cccgaagtca cctgcgtcgt ggtggatgtc agccaggaag atcccgaggt gcagttcaac    900
tggtacgtgg acggagtgga ggtgcataac gccaaaacca agcccaggga gagcagttc     960
aacagcacct atcgggtcgt gtccgtgctc accgtcctgc atcaggattg gctcaacggc   1020
aaggagtaca agtgcaaggt gtccaacaag ggcctgccct cctccatcga aagaccatc    1080
tccaaggcta agggccaacc tcgggagccc caagtgtata ccctccctcc cagccaggag   1140
gagatgacca gaatcaagt gagcctgacc tgcctcgtga agggatttta ccctccgac    1200
atcgctgtgg aatgggaaag caatggccaa cctgagaaca actacaagac cacacccccc   1260
gtgctggact ccgatggctc cttcttcctg tacagcaggc tgaccgtgga caaatcccgg   1320
tggcaagagg gaaacgtgtt cagctgctcc gtgatgcacg aggctctcca caaccactac   1380
acccagaaga gcctctccct gagcctcggc tagtaa                              1416
```

<210> SEQ ID NO 20
<211> LENGTH: 234
<212> TYPE: PRT
<213> ORGANISM: Artificial Sequence
<220> FEATURE:
<223> OTHER INFORMATION: light chain 6665; PP10760 L; PP10763 L; PP10766 L

<400> SEQUENCE: 20

```
Met Glu Thr Asp Thr Leu Leu Leu Trp Val Leu Leu Leu Trp Val Pro
1               5                   10                  15
Gly Ser Thr Gly Asp Ile Gln Met Thr Gln Ser Pro Ser Ser Leu Ser
            20                  25                  30
Ala Ser Val Gly Asp Arg Val Thr Ile Thr Cys Gln Ala Ser Glu Asp
        35                  40                  45
Ile Tyr Asp Arg Leu Ala Trp Tyr Gln Gln Lys Pro Gly Lys Ala Pro
    50                  55                  60
Lys Leu Leu Ile Ser Gly Ala Thr Ser Leu Glu Thr Gly Val Pro Ser
65                  70                  75                  80
Arg Phe Ser Gly Ser Gly Ser Gly Thr Asp Tyr Thr Phe Thr Ile Ser
                85                  90                  95
Ser Leu Gln Pro Glu Asp Ile Ala Thr Tyr Tyr Cys Gln Gln Tyr Trp
            100                 105                 110
Ser Val Pro Trp Thr Phe Gly Gly Gly Thr Lys Val Glu Ile Lys Arg
        115                 120                 125
Thr Val Ala Ala Pro Ser Val Phe Ile Phe Pro Pro Ser Asp Glu Gln
    130                 135                 140
Leu Lys Ser Gly Thr Ala Ser Val Val Cys Leu Leu Asn Asn Phe Tyr
145                 150                 155                 160
Pro Arg Glu Ala Lys Val Gln Trp Lys Val Asp Asn Ala Leu Gln Ser
                165                 170                 175
Gly Asn Ser Gln Glu Ser Val Thr Glu Gln Asp Ser Lys Asp Ser Thr
            180                 185                 190
Tyr Ser Leu Ser Ser Thr Leu Thr Leu Ser Lys Ala Asp Tyr Glu Lys
        195                 200                 205
His Lys Val Tyr Ala Cys Glu Val Thr His Gln Gly Leu Ser Ser Pro
    210                 215                 220
Val Thr Lys Ser Phe Asn Arg Gly Glu Cys
225                 230
```

<210> SEQ ID NO 21
<211> LENGTH: 107
<212> TYPE: PRT
<213> ORGANISM: Artificial Sequence
<220> FEATURE:
<223> OTHER INFORMATION: VL6665; PP10760 VL; PP10763 VL; PP10766 VL

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asp Ile Tyr Asp Arg
            20                  25                  30

Leu Ala Trp Tyr Gln Gln Lys Pro Gly Lys Ala Pro Lys Leu Leu Ile
        35                  40                  45

Ser Gly Ala Thr Ser Leu Glu Thr Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Tyr Trp Ser Val Pro Trp
                85                  90                  95

Thr Phe Gly Gly Gly Thr Lys Val Glu Ile Lys
            100                 105

<210> SEQ ID NO 22
<211> LENGTH: 705
<212> TYPE: DNA
<213> ORGANISM: Artificial Sequence
<220> FEATURE:
<223> OTHER INFORMATION: light chain 6665 nucleotide; PP10760 L
      nucleotide; PP10763 L nucleotide; PP10766 L nucleotide

<400> SEQUENCE: 22
atggagaccg acaccctgct gctctgggtg ctgctgctct gggtgcccgg ctccaccgga     60
gacatccaga tgacccagag ccccagcagc ctgagcgcca gcgtgggcga cagggtgacc    120
atcacctgcc aggcctccga ggacatctac gacaggctgg cctggtatca gcagaagccc    180
ggcaaggccc ccaaacttct gatctcaggg gccaccagct tggagaccgg cgtgcctagc    240
aggttcagcg gcagcggtag tggcaccgac tacaccttca ccatcagctc cctgcagccc    300
gaggatatcg ccacctacta ctgccagcag tattggagcg tgccatggac cttcggtggc    360
ggaactaagg tggagatcaa gcggaccgtg gccgccccca gcgtgttcat cttccctccc    420
agcgacgagc agctgaagtc tggcaccgcc agcgtggtgt gcctgctgaa caacttctac    480
ccccgcgagg ccaaggtgca gtggaaggtg gacaacgccc tgcagagcgg caacagccag    540
gagagcgtga ccgagcagga ctccaaggac agcacctaca gcctgagcag caccctgacc    600
ctgagcaagg ccgactacga gaagcacaag gtgtacgcct gcgaggtgac ccaccaggga    660
ctgtctagcc ccgtgaccaa gagcttcaac cggggcgagt gctaa              705

<210> SEQ ID NO 23
<211> LENGTH: 234
<212> TYPE: PRT
<213> ORGANISM: Artificial Sequence
<220> FEATURE:
<223> OTHER INFORMATION: light chain 6666; PP10761 L; PP10764 L; PP10767
      L

<400> SEQUENCE: 23

Met Glu Thr Asp Thr Leu Leu Leu Trp Val Leu Leu Leu Trp Val Pro

```
             1               5                  10                 15
         Gly Ser Thr Gly Asp Ile Gln Met Thr Gln Ser Pro Ser Ser Leu Ser
                         20                 25                 30
         Ala Ser Val Gly Asp Arg Val Thr Ile Thr Cys Gln Ala Ser Glu Asp
                         35                 40                 45
         Ile Tyr Asp Arg Leu Ala Trp Tyr Gln Gln Lys Pro Gly Lys Ala Pro
          50                 55                 60
         Lys Leu Leu Ile Ser Gly Ala Thr Ser Leu Glu Thr Gly Val Pro Ser
         65                  70                 75                  80
         Arg Phe Ser Gly Ser Gly Ser Gly Lys Asp Tyr Thr Phe Thr Ile Ser
                         85                 90                 95
         Ser Leu Gln Pro Glu Asp Ile Ala Thr Tyr Tyr Cys Gln Gln Tyr Trp
                        100                105                110
         Ser Val Pro Trp Thr Phe Gly Gly Gly Thr Lys Val Glu Ile Lys Arg
                        115                120                125
         Thr Val Ala Ala Pro Ser Val Phe Ile Phe Pro Pro Ser Asp Glu Gln
         130                135                140
         Leu Lys Ser Gly Thr Ala Ser Val Val Cys Leu Leu Asn Asn Phe Tyr
         145                150                155                160
         Pro Arg Glu Ala Lys Val Gln Trp Lys Val Asp Asn Ala Leu Gln Ser
                        165                170                175
         Gly Asn Ser Gln Glu Ser Val Thr Glu Gln Asp Ser Lys Asp Ser Thr
                        180                185                190
         Tyr Ser Leu Ser Ser Thr Leu Thr Leu Ser Lys Ala Asp Tyr Glu Lys
                        195                200                205
         His Lys Val Tyr Ala Cys Glu Val Thr His Gln Gly Leu Ser Ser Pro
         210                215                220
         Val Thr Lys Ser Phe Asn Arg Gly Glu Cys
         225                230

<210> SEQ ID NO 24
<211> LENGTH: 107
<212> TYPE: PRT
<213> ORGANISM: Artificial Sequence
<220> FEATURE:
<223> OTHER INFORMATION: VL6666; PP10761 VL; PP10764 VL; PP10767 VL

<400> SEQUENCE: 24

Asp Ile Gln Met Thr Gln Ser Pro Ser Ser Leu Ser Ala Ser Val Gly
 1               5                  10                 15
Asp Arg Val Thr Ile Thr Cys Gln Ala Ser Glu Asp Ile Tyr Asp Arg
                20                  25                 30
Leu Ala Trp Tyr Gln Gln Lys Pro Gly Lys Ala Pro Lys Leu Leu Ile
             35                 40                 45
Ser Gly Ala Thr Ser Leu Glu Thr Gly Val Pro Ser Arg Phe Ser Gly
     50                  55                 60
Ser Gly Ser Gly Lys Asp Tyr Thr Phe Thr Ile Ser Ser Leu Gln Pro
65                  70                 75                  80
Glu Asp Ile Ala Thr Tyr Tyr Cys Gln Gln Tyr Trp Ser Val Pro Trp
                85                 90                 95
Thr Phe Gly Gly Gly Thr Lys Val Glu Ile Lys
            100                105

<210> SEQ ID NO 25
<211> LENGTH: 705
<212> TYPE: DNA
```

<213> ORGANISM: Artificial Sequence
<220> FEATURE:
<223> OTHER INFORMATION: light chain 6666 nucleotide; PP10761 L nucleotide; PP10764 L nucleotide; PP10767 L nucleotide

<400> SEQUENCE: 25

```
atggagaccg acaccctgct gctctgggtg ctgctgctct gggtgcccgg ctccaccgga    60
gacatccaga tgacccagag ccccagcagc ctgagcgcca gcgtgggcga cagggtgacc   120
atcacctgcc aggcctccga ggacatctac gacaggctgg cctggtatca gcagaagccc   180
ggcaaggccc ccaaacttct gatctcaggg gccaccagct ggagaccggc gtgcctagc    240
aggttcagcg gcagcggtag tggcaaggac tacaccttca ccatcagctc cctgcagccc   300
gaggatatcg ccacctacta ctgccagcag tattggagcg tgccatggac cttcggtggc   360
ggaactaagg tggagatcaa gcggaccgtg gccgccccca gcgtgttcat cttccctccc   420
agcgacgagc agctgaagtc tggcaccgcc agcgtggtgt gcctgctgaa caacttctac   480
ccccgcgagg ccaaggtgca gtggaaggtg acaacgccc tgcagagcgg caacagccag   540
gagagcgtga ccgagcagga ctccaaggac agcacctaca gcctgagcag caccctgacc   600
ctgagcaagg ccgactacga aaagcacaag gtgtacgcct gcgaggtgac ccaccaggga   660
ctgtctagcc ccgtgaccaa gagcttcaac cggggcgagt gctaa               705
```

<210> SEQ ID NO 26
<211> LENGTH: 234
<212> TYPE: PRT
<213> ORGANISM: Artificial Sequence
<220> FEATURE:
<223> OTHER INFORMATION: light chain 6667; PP10762 L; PP10765 L; PP10768 L

<400> SEQUENCE: 26

```
Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Glu Asp
        35                  40                  45

Ile Tyr Asp Arg Leu Ala Trp Tyr Gln Gln Lys Pro Gly Lys Ala Pro
    50                  55                  60

Asn Leu Leu Val Ser Gly Ala Thr Ser Leu Glu Ser Gly Val Pro Ser
65                  70                  75                  80

Arg Phe Ser Gly Ser Gly Ser Lys Asp Tyr Thr Leu Thr Ile Ser
                85                  90                  95

Ser Leu Gln Pro Glu Asp Phe Ala Thr Tyr Tyr Cys Gln Gln Tyr Trp
            100                 105                 110

Ser Val Pro Trp Thr Phe Gly Gly Gly Thr Lys Val Glu Ile Lys Arg
        115                 120                 125

Thr Val Ala Ala Pro Ser Val Phe Ile Phe Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
```

```
            195                 200                 205
His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 27
<211> LENGTH: 107
<212> TYPE: PRT
<213> ORGANISM: Artificial Sequence
<220> FEATURE:
<223> OTHER INFORMATION: VL6667; PP10762 VL; PP10765 VL; PP10768 VL

<400> SEQUENCE: 27

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Ile Tyr Asp Arg
            20                  25                  30

Leu Ala Trp Tyr Gln Gln Lys Pro Gly Lys Ala Pro Asn Leu Leu Val
        35                  40                  45

Ser Gly Ala Thr Ser Leu Glu Ser Gly Val Pro Ser Arg Phe Ser Gly
    50                  55                  60

Ser Gly Ser Gly Lys Asp Tyr Thr Leu Thr Ile Ser Ser Leu Gln Pro
65                  70                  75                  80

Glu Asp Phe Ala Thr Tyr Tyr Cys Gln Gln Tyr Trp Ser Val Pro Trp
                85                  90                  95

Thr Phe Gly Gly Gly Thr Lys Val Glu Ile Lys
            100                 105
```

<210> SEQ ID NO 28
<211> LENGTH: 705
<212> TYPE: DNA
<213> ORGANISM: Artificial Sequence
<220> FEATURE:
<223> OTHER INFORMATION: light chain 6667 nucleotide; PP10762 L
      nucleotide; PP10765 L nucleotide; PP10768 L nucleotide

<400> SEQUENCE: 28

```
atggagaccg acaccctgct gctctgggtg ctgctgctct gggtgcccgg ctccaccgga      60
gacatccaga tgacccagag ccccagcagc ctgagcgcca gcgtgggcga cagggtgacc     120
atcacctgca gggcctccga ggacatctac gacaggctgg cctggtatca gcagaagccc     180
ggcaaggccc ccaatcttct ggtctcaggg gccaccagct ggagagcggg cgtgcctagc     240
aggttcagcg gcagcggtag tggcaaggac tacaccctca ccatcagctc cctgcagccc     300
gaggatttcg ccacctacta ctgccagcag tattggagcg tgccatggac cttcggtggc     360
ggaactaagg tggagatcaa gcggaccgtg gccgccccca gcgtgttcat cttccctccc     420
agcgacgagc agctgaagtc tggcaccgcc agcgtggtgt gcctgctgaa caacttctac     480
ccccgcgagg ccaaggtgca gtggaaggtg gacaacgccc tgcagagcgg caacagccag     540
gagagcgtga ccgagcagga ctccaaggac agcacctaca gcctgagcag caccctgacc     600
ctgagcaagg ccgactacga gaagcacaag gtgtacgcct gcgaggtgac ccaccaggga     660
ctgtctagcc ccgtgaccaa gagcttcaac cggggcgagt gctaa                    705
```

<210> SEQ ID NO 29
<211> LENGTH: 113
<212> TYPE: PRT
<213> ORGANISM: Artificial Sequence

```
<220> FEATURE:
<223> OTHER INFORMATION: VH gemline donor

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Lys Gly Arg
            20                  25                  30

Phe Thr Ile Ser Arg Asp Asn Ser Lys Asn Thr Leu Tyr Leu Gln Met
        35                  40                  45

Asn Ser Leu Arg Ala Glu Asp Thr Ala Val Tyr Tyr Cys Ala Lys Tyr
    50                  55                  60

Phe Asp Tyr Trp Gly Gln Gly Thr Leu Val Thr Val Ser Ser Ser Ser
65              70                  75                  80

Tyr Ala Met Ser Met Val Arg Gln Ala Pro Gly Lys Gly Leu Glu Trp
                85                  90                  95

Val Ser Ala Ile Ser Gly Ser Gly Gly Ser Thr Tyr Tyr Ala Asp Ser
            100                 105                 110

Val

<210> SEQ ID NO 30
<211> LENGTH: 107
<212> TYPE: PRT
<213> ORGANISM: Artificial Sequence
<220> FEATURE:
<223> OTHER INFORMATION: VL gemline donor

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65              70                  75                  80

Glu Asp Ile Ala Thr Tyr Tyr Cys Gln Gln Tyr Asp Asn Leu Pro Leu
                85                  90                  95

Thr Phe Gly Gly Gly Thr Lys Val Glu Ile Lys
            100                 105
```

ANTI-IL-17A ANTIBODIES AND USE THEREOF

CROSS-REFERENCE TO RELATED APPLICATIONS

This application is a National Stage Application and claims priority under 35 U.S.C. § 371 to Patent Cooperation Treaty application PCT/CN2019/098327, filed Jul. 30, 2019, which claims the benefit of Patent Cooperation Treaty application PCT/CN2018/097795, filed Jul. 31, 2018. Priority is claimed to these applications and the disclosures of these prior applications are considered part of the disclosure of this application and to the extent allowed the entire contents of the aforementioned applications are incorporated herein.

SEQUENCE LISTING

This application incorporates by reference in its entirety the Sequence Listing entitled "20240528-262790-483470AmendedSequenceListing.XML", is 46,709 bytes in size and was created on May 28, 2024, and filed electronically herewith.

BACKGROUND OF THE INVENTION

IL-17A (Interleukin-17A) is a protein encoded by the IL-17A gene. The IL-17A protein is a glycoprotein that can form either a disulfide-linked homodimer or a heterodimer with the IL-17F protein. IL-17A is a pro-inflammatory cytokine that acts on a variety of cells (e.g., fibroblasts, epithelial cells, endothelial cells, and monocytes) to induce the production of other cytokines, including IL-6, and tumor necrosis factor-α (TNFα) (Eyerich et al., 2010; Iwakura et al., 2011).

Previous studies have shown that agonistic antibodies of IL-17A could enhance the killing ability of T cells in a mouse model. However, there is still a strong need for IL-17A antibodies with better performances.

SUMMARY OF THE INVENTION

The present disclosure provides an antibody or an antigen binding fragment thereof, which is capable of binding to IL-17A and could exhibit at least one of the following properties: 1) having a high affinity to IL-17; 2) specifically binding to IL-17A, and does not substantially bind to IL-17B, IL-17C, IL-17D, IL-17E or IL-17F; 3) blocking an interaction between IL-17A and IL-17R (e.g., IL-17RA domain, and/or IL-17RC domain); 4) neutralizing IL-17A in vivo; 5) capable of treating an autoimmune disease or disorder. In addition, the present disclosure also provides a method for preparing and/or using the antibody or the antigen binding fragment thereof.

In one aspect, the present disclosure provides an antibody or an antigen binding fragment thereof, which binds to IL-17A and exhibits at least one of the following properties: 1) binds to IL-17A with a $K_D$ of $2\times10^{-9}$ M or less, as measured by Octet; 2) specifically binds to IL-17A, and does not substantially bind to IL-17B, IL-17C, IL-17D, IL-17E, or IL-17F; 3) blocks san interaction between IL-17A and IL-17R (such as IL-17RA and/or IL-17RC); 4) neutralized IL-17A in vivo; and 5) is capable of treating an autoimmune disease or disorder.

In some embodiments, the antibody is selected from the group consisting of: a monoclonal antibody, a chimeric antibody, a humanized antibody, a fully human antibody and a bispecific antibody.

In some embodiments, the antigen binding fragment is selected from the group consisting of: a Fab fragment, a Fab' fragment, a $F(ab)_2$ fragment, a Fv fragment, and a ScFv.

In some embodiments, the antibody or the antigen binding fragment thereof competes with a reference antibody. The reference antibody comprises: 1) light chain CDR1-3 comprising an amino acid sequence as set forth in SEQ ID NO: 4-6 respectively, and heavy chain CDR 1-3 comprising an amino acid sequence as set forth in SEQ ID NO: 1-3 respectively; 2) a light chain variable region comprising an amino acid sequence as set forth in SEQ ID NO: 8, and a heavy chain variable region comprising an amino acid sequence as set forth in SEQ ID NO: 7; 3) a light chain variable region comprising an amino acid sequence as set forth in SEQ ID NO: 21, and a heavy chain variable region comprising an amino acid sequence as set forth in SEQ ID NO: 12; 4) a light chain variable region comprising an amino acid sequence as set forth in SEQ ID NO: 24, and a heavy chain variable region comprising an amino acid sequence as set forth in SEQ ID NO: 12; 5) a light chain variable region comprising an amino acid sequence as set forth in SEQ ID NO: 27, and a heavy chain variable region comprising an amino acid sequence as set forth in SEQ ID NO: 12; 6) a light chain variable region comprising an amino acid sequence as set forth in SEQ ID NO:21, and a heavy chain variable region comprising an amino acid sequence as set forth in SEQ ID NO: 15; 7) a light chain variable region comprising an amino acid sequence as set forth in SEQ ID NO: 24, and a heavy chain variable region comprising an amino acid sequence as set forth in SEQ ID NO: 15; 8) a light chain variable region comprising an amino acid sequence as set forth in SEQ ID NO: 27, and a heavy chain variable region comprising an amino acid sequence as set forth in SEQ ID NO: 15; 9) a light chain variable region comprising an amino acid sequence as set forth in SEQ ID NO: 21, and a heavy chain variable region comprising an amino acid sequence as set forth in SEQ ID NO: 18; 10) a light chain variable region comprising an amino acid sequence as set forth in SEQ ID NO: 24, and a heavy chain variable region comprising an amino acid sequence as set forth in SEQ ID NO: 18; or 11) a light chain variable region comprising an amino acid sequence as set forth in SEQ ID NO: 27, and a heavy chain variable region comprising an amino acid sequence as set forth in SEQ ID NO: 18.

In some embodiments, the antibody comprises a light chain or a fragment thereof. The light chain or a fragment thereof comprises a light chain CDR1, and the light chain CDR1 comprises an amino acid sequence as set forth in SEQ ID NO: 4. In some embodiments, the light chain or a fragment thereof comprises a light chain CDR2, and the light chain CDR2 comprises an amino acid sequence as set forth in SEQ ID NO: 5. SEQ ID NO: 5 is a short amino acid sequence comprised of the following 3 amino acids, "gly ala thr" this is an artificial sequence that is an LCDR2. In some embodiments, the light chain or a fragment thereof comprises a light chain CDR3, and the light chain CDR3 comprises an amino acid sequence as set forth in SEQ ID NO: 6.

In some embodiments, the light chain or a fragment thereof comprises a light chain variable region and said light chain variable region comprises an amino acid sequence selected from SEQ ID NO: 8, SEQ ID NO: 21, SEQ ID NO: 24 and SEQ ID NO: 27.

In some embodiments, the light chain or a fragment thereof comprises a light chain constant region, and the light chain constant region comprises a human Igκ constant region.

In some embodiments, the light chain or a fragment thereof comprises an amino acid sequence selected from SEQ ID NO: 10, SEQ ID NO: 20, SEQ ID NO: 23 and SEQ ID NO: 26.

In some embodiments, the antibody comprises a heavy chain or a fragment thereof. The heavy chain or a fragment thereof comprises a heavy chain CDR1, and the heavy chain CDR1 comprises an amino acid sequence as set forth in SEQ ID NO: 1. In some embodiments, the heavy chain or a fragment thereof comprises a heavy chain CDR2, and the heavy chain CDR2 comprises an amino acid sequence as set forth in SEQ ID NO: 2. In some embodiments, the heavy chain or a fragment thereof comprises a heavy chain CDR3, and the heavy chain CDR3 comprises an amino acid sequence as set forth in SEQ ID NO: 3.

In some embodiments, the heavy chain or a fragment thereof comprises a heavy chain variable region, and the heavy chain variable region comprises an amino acid sequence selected from SEQ ID NO: 7, SEQ ID NO: 12, SEQ ID NO: 15 and SEQ ID NO: 18.

In some embodiments, the heavy chain or a fragment thereof comprises a heavy chain constant region, and the heavy chain constant region comprises a human IgG constant region. In some embodiments, the human IgG constant region comprises an IgG4 constant region.

In some embodiments, the heavy chain or a fragment thereof comprises an amino acid sequence selected from SEQ ID NO: 9, SEQ ID NO: 11, SEQ ID NO: 14 and SEQ ID NO: 17.

In some embodiments, the IL-17A is selected from the group consisting of: a human IL-17A, a mouse IL-17A and a monkey IL-17A (such as a cynomolgus monkey IL-17A).

In some embodiments, the antibody or the antigen binding fragment thereof binds to human IL-17A and cynomolgus monkey IL-17A, but not substantially to mouse IL-17A.

In some embodiments, the antibody or the antigen binding fragment thereof comprising: 1) light chain CDR1-3 comprising an amino acid sequence as set forth in SEQ ID NO: 4-6 respectively, and heavy chain CDR 1-3 comprising an amino acid sequence as set forth in SEQ ID NO: 1-3 respectively; 2) a light chain variable region comprising an amino acid sequence as set forth in SEQ ID NO: 8, and a heavy chain variable region comprising an amino acid sequence as set forth in SEQ ID NO: 7; 3) a light chain variable region comprising an amino acid sequence as set forth in SEQ ID NO: 21, and a heavy chain variable region comprising an amino acid sequence as set forth in SEQ ID NO: 12; 4) a light chain variable region comprising an amino acid sequence as set forth in SEQ ID NO: 24, and a heavy chain variable region comprising an amino acid sequence as set forth in SEQ ID NO: 12; 5) a light chain variable region comprising an amino acid sequence as set forth in SEQ ID NO: 27, and a heavy chain variable region comprising an amino acid sequence as set forth in SEQ ID NO: 12; 6) a light chain variable region comprising an amino acid sequence as set forth in SEQ ID NO: 21, and a heavy chain variable region comprising an amino acid sequence as set forth in SEQ ID NO: 15; 7) a light chain variable region comprising an amino acid sequence as set forth in SEQ ID NO: 24, and a heavy chain variable region comprising an amino acid sequence as set forth in SEQ ID NO: 15; 8) a light chain variable region comprising an amino acid sequence as set forth in SEQ ID NO: 27, and a heavy chain variable region comprising an amino acid sequence as set forth in SEQ ID NO: 15; 9) a light chain variable region comprising an amino acid sequence as set forth in SEQ ID NO: 21, and a heavy chain variable region comprising an amino acid sequence as set forth in SEQ ID NO: 18; 10) a light chain variable region comprising an amino acid sequence as set forth in SEQ ID NO: 24, and a heavy chain variable region comprising an amino acid sequence as set forth in SEQ ID NO: 18; or 11) a light chain variable region comprising an amino acid sequence as set forth in SEQ ID NO: 27, and a heavy chain variable region comprising an amino acid sequence as set forth in SEQ ID NO: 18.

In another aspect, the present disclosure provides a fusion protein comprising the antibody or the antigen binding fragment thereof according to the present disclosure.

In another aspect, the present disclosure provides an isolated nucleic acid molecule or molecules, encoding for the antibody or the antigen binding fragment thereof, or the fusion protein according to the present disclosure.

In another aspect, the present disclosure provides a vector or vectors, comprising the isolated nucleic acid molecule or molecules according to the present disclosure.

In another aspect, the present disclosure provides a cell, comprising the isolated nucleic acid molecule or molecules, or the vector or vectors according to the present disclosure.

In another aspect, the present disclosure provides a method for producing the antibody or the antigen binding fragment thereof, or the fusion protein according to the present disclosure, comprising culturing the cell of the present disclosure under conditions enabling expression of the antibody or the antigen binding fragment thereof, or the fusion protein. In some embodiments, the method optionally further comprises harvesting said antibody or the antigen binding fragment thereof or said fusion protein.

In another aspect, the present disclosure provides a composition, comprising the antibody or the antigen binding fragment thereof, the fusion protein, the isolated nucleic acid molecule or molecules, the vector or vectors, and/or the cell according to the present disclosure, and optionally a pharmaceutically acceptable excipient. In some embodiments, the composition further comprises an additional therapeutically active ingredient.

In another aspect, the present disclosure provides a use of the antibody or the antigen binding fragment thereof, the fusion protein, the isolated nucleic acid molecule or molecules, the vector or vectors, and/or the cell according to the present disclosure in the manufacture of a medicament for preventing and/or treating a disease or disorder associated with an inappropriate expression or function of IL-17A. The disease or disorder may be an autoimmune disease or disorder. For example, the disease or disorder may comprise psoriasis and/or arthritis (e.g. rheumatoid arthritis (RA)). In another aspect, the present disclosure provides a use of the antibody or the antigen binding fragment thereof, or the fusion protein according to the present disclosure in the manufacture of an agent for determining the presence and/or amount of IL-17A in a sample.

In another aspect, the present disclosure provides a method for preventing and/or treating a disease or disorder in a subject in need thereof, comprising administering to said subject an effective amount of the antibody or the antigen binding fragment thereof, the fusion protein, the isolated nucleic acid molecule or molecules, the vector or vectors, and/or the cell according to the present disclosure, wherein said disease or disorder is a disease or disorder associated with an inappropriate expression or function of IL-17A. The disease or disorder may be an autoimmune disease or disorder. For example, the disease or disorder may comprise psoriasis and/or arthritis (e.g. rheumatoid arthritis (RA)).

In another aspect, the present disclosure provides a method for determining the presence and/or amount of IL-17A in a sample, comprising: a) contacting said sample with the antibody or the antigen binding fragment thereof, or the fusion protein according to the present disclosure; and b) determining the presence and/or amount of said antibody, said antigen binding fragment thereof, or said fusion protein bound to said sample.

In another aspect, the present disclosure provides the antibody or the antigen binding fragment thereof, the fusion protein, the isolated nucleic acid molecule or molecules, the vector or vectors, or the cell according to the present disclosure, for a) preventing and/or treating a disease or disorder, and/or b) determining the presence and/or amount of IL-17A in a sample, wherein said disease or disorder is a disease or disorder associated with an inappropriate expression or function of IL-17A. The disease or disorder may be an autoimmune disease or disorder. For example, the disease or disorder may comprise psoriasis and/or arthritis (e.g. rheumatoid arthritis (RA).

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are employed, and the accompanying drawings (also "figure" and "FIG." herein), of which:

FIG. 1 illustrates the amino acid sequence alignment of VH and VL of the antibodies of the present disclosure.

DETAILED DESCRIPTION

Figure 2A:
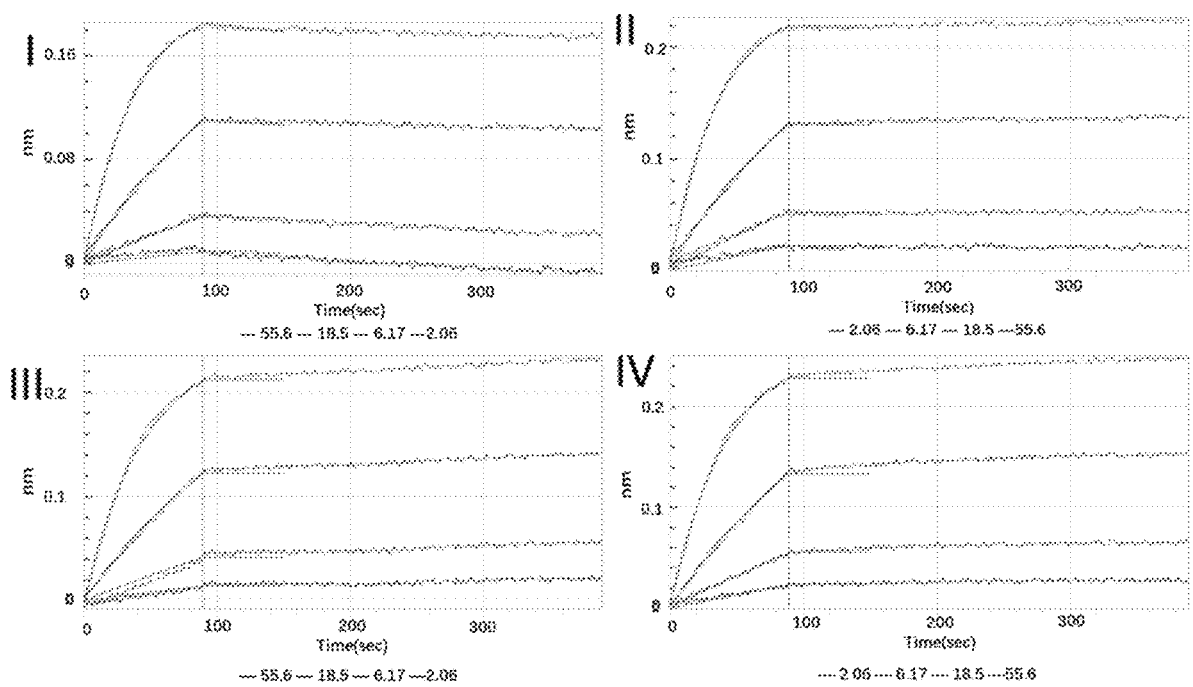
FIG. 2 illustrates the binding affinity of the antibodies of the present disclosure, as measured by Octet.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "antibody", as used herein, generally refers to an immunoglobulin or an immunoglobulin-like molecule capable of specifically recognizing or binding to an antigen. An antibody may comprise a light chain (L) and a heavy chain (H). The light chains of an antibody can be classified as κ and λ light chains. The heavy chains can be classified as μ, δ, γ, α or ε, and the isotypes of an antibody are defined as IgM, IgD, IgG (e.g., IgG1, IgG2, IgG3 or IgG4 subtype), IgA and IgE, respectively. Each heavy chain may comprise a heavy chain variable region (VH) and a heavy chain constant region (CH). The heavy chain constant region may comprise three domains (CH1, CH2 and CH3). Each light chain may comprise a light chain variable region (VL) and a light chain constant region (CL). The light chain constant region may comprise a CL domain. The VH and VL regions can also be subdivided into regions with high variability known as complementarity determining regions (CDRs) interspersed with more conserved regions known as framework regions (FRs). Each VH and VL consists of 3 CDRs and 4 FRs arranged from N-terminal to C-terminal in the following order: FR1, CDR1, FR2, CDR2, FR3, CDR3, FR4. The variable regions (VH and VL) of each heavy/light chain pair form the antibody binding site, respectively. Distribution of amino acids to regions or domains follows the definition of Kabat Sequences of Proteins of Immunological Interest (*National Institutes of Health*, Bethesda, Md. (1987 and 1991)), or Chothia & Lesk (1987) *J. Mol. Biol.* 196:901-917; Chothia et al. (1989) *Nature* 342:878-883. The term "antibody" is not limited by any antibody-producing method. For example, it includes recombinant antibodies, monoclonal antibodies, and other forms of antibodies. In some cases, an antibody of the present disclosure is an isolated antibody.

The term "antigen binding fragment", as used herein, generally refers to one or more fragments of a full-length antibody that retain the ability to bind the same antigen to which the antibody binds (e.g., IL17) and/or competes against an intact antibody for an antigen-specific binding. Antigen binding fragment can be produced by recombinant DNA techniques or by enzymatic or chemical cleavage of intact antibodies. In some cases, the antigen binding site includes Fab, Fab', F (ab')$_2$, F (ab)$_2$, Fd, Fv, dAb and complementarity determining region (CDR) fragments, single chain antibodies (e.g., ScFv), chimeric antibodies, diabodies, and polypeptides that comprise at least a portion of an antibody that is sufficient to confer specific antigen-binding ability to the polypeptide.

The term "IL-17A", as used herein, generally refers to interleukin 17A, a protein encoded by the IL-17A gene. The IL-17A protein is a glycoprotein that can form either a disulfide-linked homodimer or a heterodimer with the IL-17F protein. Members of the IL-17 protein family may contain four highly conserved cysteine residues on each monomer (Kolls and Lindén, 2004; Iwakura et al., 2011). IL-17A may be secreted not only by CD4+ T cells (Th17 cells), which also produce IL-17F, IL-21, and IL-22 (Korn et al., 2009; Kurebayashi et al., 2013), but also by CD8+ T cells (Tc17 cells), γδ T cells, invariant natural killer T cells (iNKT cells), innate lymphoid cells (ILCs) including lymphoid tissue inducer cells (LTi cells), B cells, neutrophils, and other non-hematopoietic cells (Cua and Tato, 2010). In the present disclosure, an "IL-17A" may comprise a human IL-17A, a mouse IL-17A, and/or a monkey IL-17A. In the present disclosure, a IL-17A may also comprise variants or fragments of human IL-17A, mouse IL-17A and/or monkey IL-17A.

The term "IL-17R", as used herein, generally refers to interleukin 17 receptor, which may be a receptor capable of binding to IL-17A. The IL-17R may be a heteromeric complex consisting of at least IL17-RA and IL-17RC.

The term "an autoimmune disease or disorder", as used in herein, generally refers to a disease or disorder occurring when the body's immune system attack and destroys healthy body tissue by mistake.

The term "psoriasis", as used in herein, generally refers to an immune-mediated skin disease that speeds up the life cycle of skin cells.

The term "rheumatoid arthritis (RA)", as used in herein, generally refers to a disease that leads to inflammation of the joints and surrounding tissues. The symptoms of rheumatoid arthritis (RA) may include stiffness, pain, swelling or deforming of joints.

The term "binding specificity", as used herein, generally refers to an ability of one substance to bind another substance specifically, and not substantially bind to any other substance at random. For example, one protein may bind to another protein specifically due to their specific structures. Binding specificity may be measured by, e.g., cross-competing assays or other binding assays known in the art.

The term "not substantially bind", as used herein, generally refers to little or almost no binding to a particular substance. For example, very few or almost no (e.g., less than 10%, less than 9%, less than 8%, less than 7%, less than 6%, less than 5%, less than 4%, less than 3%, less than 2%, less than 1%, less than 0.5%, less than 0.1%, or less than 0.01%) antibody, or the antigen binding fragment thereof of the present disclosure may bind to IL-17B, IL-17C, IL-17D, IL-17E, or IL-17F.

The term "$K_D$", as used herein, generally refers to the dissociation constant, a specific type of equilibrium constant that measures the propensity of a larger object to separate (dissociate) reversibly into smaller components, as when a complex falls apart into its component molecules. The dissociation constant is the inverse of the association constant. In the specific case of antibodies (Ab) binding to antigen (Ag), usually the term affinity constant refers to the association constant.

The term "monoclonal antibody", as used herein, generally refers to antibodies that are made by identical immune cells that are all clones of a unique parent cell. Monoclonal antibodies can have a monovalent affinity, in that they bind to the same epitope (the part of an antigen that is recognized by the antibody). It has become an important tool in biochemistry, molecular biology, and medicine. Several monoclonal antibody technologies had been developed recently, such as phage display, single B cell culture, single cell amplification from various B cell populations and single plasma cell interrogation technologies.

The term "chimeric antibody", as used herein, generally refers to an antibody in which the Variable (V) region of light and heavy chains is of mouse origin, while the Constant (C) region is of human origin. In general, the chimeric antibody may retain the specificity and affinity of the original mouse monoclonal antibody, but HAMA response may be significantly reduced.

The term "humanized antibody", as used herein, generally refers to antibodies from non-human species whose protein sequences have been modified to increase their similarity to antibody variants produced naturally in humans. The amino acid sequence of a humanized antibody may be essentially identical to that of a human variant, despite the non-human origin of some of its complementarity determining region (CDR) segments responsible for the ability of the antibody to bind to its target antigen.

The term "fully human antibody", as used herein, generally refers to an antibody with fully human amino acid sequence derived antibody region therapeutics where antigen specificity has been selected either in vivo by the use of genetically modified mice or by antibody engineering processes combined with screening.

The term "bispecific antibody", as used herein, generally refers to an artificial protein that can simultaneously bind to two different types of antigen. The main types of manufacturing methods are quadromas, chemical conjugation, and genetic recombination. IgG-like format retains the traditional monoclonal antibody (mAb) structure of two Fab arms and one Fc region, except the two Fab sites bind different antigens. Each heavy and light chain pair is from a unique mAb. The Fc region made from the two heavy chains forms the third binding site. Non-IgG-like format includes chemically linked Fabs, consisting of only the Fab regions, and various types of bivalent and trivalent single-chain variable fragments (ScFvs). There are also fusion proteins mimicking the variable domains of two antibodies.

The term "Fab fragment", as used herein, generally refers to a portion (such as an antigen-binding fragment) of an immunoglobulin molecule. A Fab fragment may comprise one light chain and part of a heavy chain with a single antigen-binding site. A Fab fragment may be obtained by papain digestion of an immunoglobulin molecule. For example, a Fab fragment may be composed of one constant and one variable domain of each of the heavy and the light chain. The variable domain may contain the paratope (the antigen-binding site), comprising a set of the complementarity determining regions, at the amino-terminal end of the immunoglobulin molecule. The enzyme papain may be used to cleave an immunoglobulin molecule into two Fab fragments and one Fc fragment. The enzyme pepsin cleaves below the hinge region, so a $F(ab')_2$ fragment and a pFc' fragment is formed. Divalent $F(ab)_2$ or $F(ab')_2$ fragments have two antigen binding regions that are linked by disulfide bonds. Reduction of $F(ab)_2$ or $F(ab')_2$ fragments produces 2 monovalent Fab or Fab' fragments, which have a free sulfhydryl group that is useful for conjugation to other molecules.

The term "Fv fragment", as used herein, generally refers to the smallest fragment made from enzymatic cleavage of IgG and IgM class antibodies. Fv fragments have the antigen-binding site made of the VH and VL regions, but they lack the CH1 and CL regions. The VH and VL chains may be held together in Fv fragments by non-covalent interactions.

The term "ScFv", as used herein, generally refers to a single-chain antibody fragment. An ScFv may be a recombinant single chain polypeptide molecule in which light and heavy chain variable regions of an antibody are connected, either directly or via a peptide linker. Single chain antibodies (ScFv) generally do not include portions of the Fc region of antibody, although methods are known for adding such regions to known ScFv molecules if desired. See Helfrich et al., *A rapid and versatile method for harnessing ScFv antibody fragments with various biological functions. J Immunol Methods* 237: 131-145 (2000) and de Haard et al., *Creating and engineering human antibodies for immunotherapy. Advanced Drug Delivery Reviews* 31:5-31 (1998).

The term "fusion protein", as used herein, generally refers to a polypeptide that comprises, or alternatively consists of, an amino acid sequence of a polypeptide fused directly or indirectly (e.g., via a linker) to an amino acid sequence of a heterologous polypeptide (i.e., a polypeptide of a different origin, sequence or structure).

The term "isolated nucleic acid molecule or molecules" as used herein, generally refers to a polymeric form of nucleotides of any length, either deoxyribonucleotides or ribonucleotides, or analogs thereof, isolated from its native environment, or that is artificially synthesized.

The term "vector or vectors" as used herein, generally refers to a nucleic acid vehicle into which a polynucleotide encoding a protein can be inserted and expressed. The genetic material elements carried in the vector can be expressed in a host cell by transforming, transducing, or transfecting the host cell with the vector. Embodiments of vectors include: plasmids; phagemids; cosmos; artificial chromosomes such as yeast artificial chromosomes (YACs), bacterial artificial chromosomes (BACs) or P1-derived artificial chromosomes (PACs); phages such as λ phage or M13 phage and animal viruses. A vector may contain a variety of elements that control expression, including promoter sequences, transcriptional initiation sequences, enhancer sequences, selection elements, and reporter genes. In addition, the vector may also contain an origin of replication. It is also possible that the vector may include components that assist its entry into the cell, such as viral particles, liposomes or protein shells, but not only these substances.

The term "cell" as used herein, generally refers to a cell that may be used to carry the vector or vectors of the present disclosure, or be used to express or produce the antibody, the antigen binding fragment of the present disclosure. A cell of the present disclosure may be a host cell. The cell may be a prokaryotic cell such as *Escherichia coli* and *Bacillus subtilis*, a fungal cell such as yeast cell or *Aspergillus* cell, an insect cell such as S2 *Drosophila* cell or Sf9, or another cell such as a CHO cell, a COS cell, an NSO cell, or other cells suitable for antibody expression.

The term "conditions enabling expression", as used herein, generally refers to conditions enabling the expression of the antibody or the antigen binding fragment thereof of the present disclosure. In some embodiments, such conditions may include but not limited to incubation time, temperature, and culture medium, and may depend on cell type and may be readily determined by a skilled arctician.

The terms "disease" and "disorder" may be used interchangeably herein, and generally refer to any condition that impairs the normal functioning of the body. Disease is often construed as a medical condition associated with specific symptoms and signs. It may be caused by external factors such as pathogens or by internal dysfunctions, particularly of the immune system, such as an immunodeficiency, or by a hypersensitivity, including allergies and autoimmunity. For example, the disease or disorder may be associated with an inappropriate expression or function of IL-17A. For example, the disease or disorder may be an autoimmune disease, such as psoriasis and/or arthritis (e.g. rheumatoid arthritis (RA)).

The term "effective amount", as used herein, generally refers to a dose sufficient to provide concentrations high enough to impart a beneficial effect on the recipient thereof. The specific therapeutically effective dose level for any particular subject will depend upon a variety of factors including the disease or disorder being treated, the severity of the disease or disorder, the activity of the specific component, the route of administration, the rate of clearance, the duration of treatment, the age, body weight, sex, diet, and general health of the subject, and other related factors.

The term "pharmaceutically acceptable excipient", as used herein, generally refers to any and all solvents, dispersion media, coatings, isotonic and absorption delaying agents, etc., that are compatible with pharmaceutical administration.

The term "inflammation reaction", as used herein, generally refers to a biological response of a subject (e.g., human or non-human animal) to an external or internal stimuli, such as pathogens, damaged cells, or irritants, and is a protective response involving at least immune cells. The signs of inflammation may include heat, pain, redness, swelling, and loss of function. Inflammation can be classified as either acute or chronic. Acute inflammation is the initial response of the body to a stimuli and may be achieved by the increased movement of plasma and leukocytes. Chronic inflammation may lead to a progressive shift in the type of cells present at the site of inflammation, such as mononuclear cells, and may be characterized by simultaneous destruction and healing of the tissue from the inflammatory process.

The term "about", as used herein, generally refers to an approximation to a given value that would reasonably be inferred based on the ordinary skill in the art, including equivalents and approximations due to the experimental and/or measurement conditions for such given value. For example, it may refer to a value that is no more than 10% above or below the value being modified by the term. For example, the term "about 5 µg/kg" means a range of 4.5 µg/kg to 5.5 µg/kg. As another example, "about 1 hour" means a range of 52 minutes to 66 minutes.

IL-17A Antibody and the Antigen Binding Fragment Thereof

In one aspect, the present disclosure provides an antibody or an antigen binding fragment thereof, which specifically binds to IL-17A.

The antibody, or the antigen binding fragment thereof may bind to IL-17A with a $K_D$ of $2\times10^{-9}$ M or less, as measured by Octet, e.g., with a $K_D$ of $1.5\times10^{-9}$ M or less, of $1\times10^{-9}$ M or less, of $9\times10^{-10}$ M or less, of $8\times10^{-10}$ M or less, of $7\times10^{-10}$ M or less, of $6\times10^{-10}$ M or less, of $5\times10^{-10}$ M or less, of $4\times10^{-10}$ M or less, of $3.5\times10^{-10}$ M or less, of $3\times10^{-10}$ M or less, of $2\times10^{-10}$ M or less, of $1\times10^{-10}$ M or less, of $1\times10^{-11}$ M or less, or of $1\times10^{-12}$ M or less.

The antibody, or the antigen binding fragment thereof may specifically bind to IL-17A, and does not substantially bind to IL-17B, IL-17C, IL-17D, IL-17E, or IL-17F.

The antibody, or the antigen binding fragment thereof may block an interaction between IL-17A and IL-17R. For example, the antibody, or the antigen binding fragment thereof may block an interaction between human IL-17A with human IL-17RA and/or human IL-17RC.

The antibody, or the antigen binding fragment thereof may bind to both human IL-17A and cynomolgus monkey IL-17A. In some cases, the antibody, or the antigen binding fragment thereof does not substantially bind to a mouse IL-17A.

For example, the IL-17A may be human IL-17A, and may be identified with Accession No. Q16552 in the UniProtKB database, or may be a variant thereof, e.g., having a sequence identity of at least 80% (e.g., at least 85%, at least 90%, at least 91%, at least 92%, at least 93%, at least 94%, at least 95%, at least 96%, at least 97%, at least 98%, at least 99% or higher) thereto.

The antibody, or the antigen binding fragment thereof may eliminate inflammation reaction when administrated to a subject in vivo.

The antibody or the antigen binding fragment thereof may neutralize IL-17A in vivo. For example, the antibody or the antigen binding fragment thereof may decrease IL-17A-induced KC secretion in the plasma by at least about 40% (e.g., at least about 40%, at least about 50%, at least about 60%, at least about 70%, at least about 80%, at least about 90% or higher), as measured in ELISA.

The antibody of the present disclosure may be a monoclonal antibody, a chimeric antibody, a humanized antibody, a fully human antibody, or a bispecific antibody. The antigen fragment may be selected from the group consisting of a Fab fragment, a Fab' fragment, a F(ab)$_2$ fragment, a Fv fragment, and a ScFv.

In the present disclosure, the antibody or the antigen binding fragment thereof may compete with a reference antibody for binding to IL-17A.

In some cases, the reference antibody comprises light chain CDR1-3 and heavy chain CDR1-3, the light chain CDR1 may comprise an amino acid sequence as set forth in SEQ ID NO: 4, the light chain CDR2 may comprise an amino acid sequence as set forth in SEQ ID NO: 5, the light chain CDR3 may comprise an amino acid sequence as set forth in SEQ ID NO: 6, the heavy chain CDR1 may comprise an amino acid sequence as set forth in SEQ ID NO: 1, the heavy chain CDR2 may comprise an amino acid sequence as set forth in SEQ ID NO: 2, and the heavy chain CDR3 may comprise an amino acid sequence as set forth in SEQ ID NO: 3.

In some cases, the reference antibody comprises a light chain variable region and a heavy chain variable region, the light chain variable region may comprise an amino acid sequence as set forth in SEQ ID NO: 8, and the heavy chain variable region may comprise an amino acid sequence as set forth in SEQ ID NO: 7.

In some cases, the reference antibody comprises a light chain variable region and a heavy chain variable region, the light chain variable region may comprise an amino acid sequence as set forth in SEQ ID NO: 21, and the heavy chain variable region may comprise an amino acid sequence as set forth in SEQ ID NO: 12.

In some cases, the reference antibody comprises a light chain variable region and a heavy chain variable region, the light chain variable region may comprise an amino acid sequence as set forth in SEQ ID NO: 24, and the heavy chain variable region may comprise an amino acid sequence as set forth in SEQ ID NO: 12.

In some cases, the reference antibody comprises a light chain variable region and a heavy chain variable region, the light chain variable region may comprise an amino acid sequence as set forth in SEQ ID NO: 27, and the heavy chain variable region may comprise an amino acid sequence as set forth in SEQ ID NO: 12.

In some cases, the reference antibody comprises a light chain variable region and a heavy chain variable region, the light chain variable region may comprise an amino acid sequence as set forth in SEQ ID NO: 21, and the heavy chain variable region may comprise an amino acid sequence as set forth in SEQ ID NO: 15.

In some cases, the reference antibody comprises a light chain variable region and a heavy chain variable region, the light chain variable region may comprise an amino acid sequence as set forth in SEQ ID NO: 24, and the heavy chain variable region may comprise an amino acid sequence as set forth in SEQ ID NO: 15.

In some cases, the reference antibody comprises a light chain variable region and a heavy chain variable region, the light chain variable region may comprise an amino acid sequence as set forth in SEQ ID NO: 27, and the heavy chain variable region may comprise an amino acid sequence as set forth in SEQ ID NO: 15.

In some cases, the reference antibody comprises a light chain variable region and a heavy chain variable region, the light chain variable region may comprise an amino acid sequence as set forth in SEQ ID NO: 21, and the heavy chain variable region may comprise an amino acid sequence as set forth in SEQ ID NO: 18.

In some cases, the reference antibody comprises a light chain variable region and a heavy chain variable region, the light chain variable region may comprise an amino acid sequence as set forth in SEQ ID NO: 24, and the heavy chain variable region may comprise an amino acid sequence as set forth in SEQ ID NO: 18.

In some cases, the reference antibody comprises a light chain variable region and a heavy chain variable region, the light chain variable region may comprise an amino acid sequence as set forth in SEQ ID NO: 27, and the heavy chain variable region may comprise an amino acid sequence as set forth in SEQ ID NO: 18.

In the present disclosure, the antibody, or the antigen binding fragment thereof may comprise a heavy chain or a fragment thereof.

For example, the heavy chain or a fragment thereof may comprise a heavy chain CDR1, and the heavy chain CDR1 may comprise an amino acid sequence as set forth in SEQ ID NO: 1. The heavy chain or a fragment thereof may comprise a heavy chain CDR2, and the heavy chain CDR2 may comprise an amino acid sequence as set forth in SEQ ID NO: 2. The heavy chain or a fragment thereof may comprise a heavy chain CDR3, and said heavy chain CDR3 comprises an amino acid sequence as set forth in SEQ ID NO: 3.

Further, the heavy chain or a fragment thereof may comprise a heavy chain variable region (VH), and the heavy chain variable region comprises an amino acid sequence selected from SEQ ID NO: 7, SEQ ID NO: 12, SEQ ID NO: 15, and SEQ ID NO: 18.

The heavy chain or a fragment thereof may comprise a heavy chain constant region. The heavy chain constant region may comprise a human IgG constant region. In some cases, the heavy chain constant region may comprise a human IgG1 constant region, a human IgG2 constant region, a human IgG3 constant region or a human IgG4 constant region. For example, the heavy chain constant region may be an IgG4 constant region.

In some cases, the heavy chain or a fragment thereof may comprise an amino acid sequence selected from SEQ ID NO: 9, SEQ ID NO: 11, SEQ ID NO: 14, and SEQ ID NO: 17.

In the present disclosure, the antibody, or the antigen binding fragment thereof may comprise a light chain or a fragment thereof.

For example, the light chain or a fragment thereof may comprise a light chain CDR1, and the light chain CDR1 may comprise an amino acid sequence as set forth in SEQ ID NO: 4. The light chain or a fragment thereof may comprise a light chain CDR2, and the light chain CDR2 may comprise an amino acid sequence as set forth in SEQ ID NO: 5. The light chain or a fragment thereof may comprise a light chain CDR3, and said light chain CDR3 comprises an amino acid sequence as set forth in SEQ ID NO: 6.

Further, the light chain or a fragment thereof may comprise a light chain variable region (VL), and the light chain variable region comprises an amino acid sequence selected from SEQ ID NO: 8, SEQ ID NO: 21, SEQ ID NO: 24 and SEQ ID NO: 27.

The light chain or a fragment thereof may comprise a light chain constant region. The light chain constant region may comprise a human Igκ constant region or a human Igλ constant region. For example, the light chain constant region may comprise a human Igκ constant region.

In some cases, the light chain or a fragment thereof may comprise an amino acid sequence selected from SEQ ID NO: 10, SEQ ID NO: 20, SEQ ID NO: 23 and SEQ ID NO: 26.

In the present disclosure, the antibody or the antigen binding fragment thereof may comprise light chain CDR1-3 and heavy chain CDR1-3, the light chain CDR1 may comprise an amino acid sequence as set forth in SEQ ID NO: 4, the light chain CDR2 may comprise an amino acid sequence as set forth in SEQ ID NO: 5, the light chain CDR3 may comprise an amino acid sequence as set forth in SEQ ID NO: 6, the heavy chain CDR1 may comprise an amino acid sequence as set forth in SEQ ID NO: 1, the heavy chain CDR2 may comprise an amino acid sequence as set forth in SEQ ID NO: 2, and the heavy chain CDR3 may comprise an amino acid sequence as set forth in SEQ ID NO: 3.

In some cases, the antibody or the antigen binding fragment thereof comprises a light chain variable region and a heavy chain variable region, the light chain variable region may comprise an amino acid sequence as set forth in SEQ ID NO: 8, and the heavy chain variable region may comprise an amino acid sequence as set forth in SEQ ID NO: 7.

In some cases, the antibody or the antigen binding fragment thereof comprises a light chain variable region and a heavy chain variable region, the light chain variable region may comprise an amino acid sequence as set forth in SEQ ID NO: 21, and the heavy chain variable region may comprise an amino acid sequence as set forth in SEQ ID NO: 12.

In some cases, the antibody or the antigen binding fragment thereof comprises a light chain variable region and a heavy chain variable region, the light chain variable region may comprise an amino acid sequence as set forth in SEQ ID NO: 24, and the heavy chain variable region may comprise an amino acid sequence as set forth in SEQ ID NO: 12.

In some cases, the antibody or the antigen binding fragment thereof comprises a light chain variable region and a heavy chain variable region, the light chain variable region may comprise an amino acid sequence as set forth in SEQ ID NO: 27, and the heavy chain variable region may comprise an amino acid sequence as set forth in SEQ ID NO: 12.

In some cases, the antibody or the antigen binding fragment thereof comprises a light chain variable region and a heavy chain variable region, the light chain variable region may comprise an amino acid sequence as set forth in SEQ ID NO: 21, and the heavy chain variable region may comprise an amino acid sequence as set forth in SEQ ID NO: 15.

In some cases, the antibody or the antigen binding fragment thereof comprises a light chain variable region and a heavy chain variable region, the light chain variable region may comprise an amino acid sequence as set forth in SEQ ID NO: 24, and the heavy chain variable region may comprise an amino acid sequence as set forth in SEQ ID NO: 15.

In some cases, the antibody or the antigen binding fragment thereof comprises a light chain variable region and a heavy chain variable region, the light chain variable region may comprise an amino acid sequence as set forth in SEQ ID NO: 27, and the heavy chain variable region may comprise an amino acid sequence as set forth in SEQ ID NO: 15.

In some cases, the antibody or the antigen binding fragment thereof comprises a light chain variable region and a heavy chain variable region, the light chain variable region may comprise an amino acid sequence as set forth in SEQ ID NO: 21, and the heavy chain variable region may comprise an amino acid sequence as set forth in SEQ ID NO: 18.

In some cases, the antibody or the antigen binding fragment thereof comprises a light chain variable region and a heavy chain variable region, the light chain variable region may comprise an amino acid sequence as set forth in SEQ ID NO: 24, and the heavy chain variable region may comprise an amino acid sequence as set forth in SEQ ID NO: 18.

In some cases, the antibody or the antigen binding fragment thereof comprises a light chain variable region and a heavy chain variable region, the light chain variable region may comprise an amino acid sequence as set forth in SEQ ID NO: 27, and the heavy chain variable region may comprise an amino acid sequence as set forth in SEQ ID NO: 18.

As another example, the antibody or the antigen binding fragment thereof may comprise LCDR1-3 and HCDR1-3 that are the same as those of the antibody PP10759-PP10768. The LCDR1-3 of the antibody PP10759-PP10768 are as set forth in SEQ ID NO: 4-6, respectively, and the HCDR1-3 of the antibody PP10759-PP10768 are as set forth in SEQ ID NO: 1-3, respectively.

As another example, the antibody or the antigen binding fragment thereof may comprise a light chain variable region and a heavy chain variable region that are the same as those of the antibody PP10759. The light chain variable region of the antibody PP10759 is as set forth in SEQ ID NO: 8, and the heavy chain variable region of the antibody PP10759 is as set forth in SEQ ID NO: 7.

As another example, the antibody or the antigen binding fragment thereof may comprise a light chain variable region and a heavy chain variable region that are the same as those of the antibody PP10760. The light chain variable region of the antibody PP10760 is as set forth in SEQ ID NO: 21, and the heavy chain variable region of the antibody PP10760 is as set forth in SEQ ID NO: 12.

As another example, the antibody or the antigen binding fragment thereof may comprise a light chain variable region and a heavy chain variable region that are the same as those of the antibody PP10761. The light chain variable region of the antibody PP10761 is as set forth in SEQ ID NO: 24, and the heavy chain variable region of the antibody PP10761 is as set forth in SEQ ID NO: 12.

As another example, the antibody or the antigen binding fragment thereof may comprise a light chain variable region and a heavy chain variable region that are the same as those of the antibody PP10762. The light chain variable region of the antibody PP10762 is as set forth in SEQ ID NO: 27, and the heavy chain variable region of the antibody PP10762 is as set forth in SEQ ID NO: 12.

As another example, the antibody or the antigen binding fragment thereof may comprise a light chain variable region and a heavy chain variable region that are the same as those of the antibody PP10763. The light chain variable region of the antibody PP10763 is as set forth in SEQ ID NO: 21, and the heavy chain variable region of the antibody PP10763 is as set forth in SEQ ID NO: 15.

As another example, the antibody or the antigen binding fragment thereof may comprise a light chain variable region and a heavy chain variable region that are the same as those of the antibody PP10764. The light chain variable region of the antibody PP10764 is as set forth in SEQ ID NO: 24, and the heavy chain variable region of the antibody PP10764 is as set forth in SEQ ID NO: 15.

As another example, the antibody or the antigen binding fragment thereof may comprise a light chain variable region and a heavy chain variable region that are the same as those of the antibody PP10765. The light chain variable region of the antibody PP10765 is as set forth in SEQ ID NO: 27, and the heavy chain variable region of the antibody PP10765 is as set forth in SEQ ID NO: 15.

As another example, the antibody or the antigen binding fragment thereof may comprise a light chain variable region and a heavy chain variable region that are the same as those of the antibody PP10766. The light chain variable region of the antibody PP10766 is as set forth in SEQ ID NO: 21, and the heavy chain variable region of the antibody PP10766 is as set forth in SEQ ID NO: 18.

As another example, the antibody or the antigen binding fragment thereof may comprise a light chain variable region and a heavy chain variable region that are the same as those of the antibody PP10767. The light chain variable region of the antibody PP10767 is as set forth in SEQ ID NO: 24, and the heavy chain variable region of the antibody PP10767 is as set forth in SEQ ID NO: 18.

As another example, the antibody or the antigen binding fragment thereof may comprise a light chain variable region and a heavy chain variable region that are the same as those of the antibody PP10768. The light chain variable region of the antibody PP10768 is as set forth in SEQ ID NO: 27, and the heavy chain variable region of the antibody PP10768 is as set forth in SEQ ID NO: 18.

As another example, the antibody or the antigen binding fragment thereof may comprise a light chain and a heavy chain that are the same as those of the antibody PP10759. The light chain of the antibody PP10759 is as set forth in SEQ ID NO: 10, and the heavy chain of the antibody PP10759 is as set forth in SEQ ID NO: 9.

As another example, the antibody or the antigen binding fragment thereof may comprise a light chain and a heavy chain that are the same as those of the antibody PP10760. The light chain of the antibody PP10760 is as set forth in SEQ ID NO: 20, and the heavy chain of the antibody PP10760 is as set forth in SEQ ID NO: 11.

As another example, the antibody or the antigen binding fragment thereof may comprise a light chain and a heavy chain that are the same as those of the antibody PP10761. The light chain of the antibody PP10761 is as set forth in SEQ ID NO: 23, and the heavy chain of the antibody PP10761 is as set forth in SEQ ID NO: 11.

As another example, the antibody or the antigen binding fragment thereof may comprise a light chain and a heavy chain that are the same as those of the antibody PP10762. The light chain of the antibody PP10762 is as set forth in SEQ ID NO: 26, and the heavy chain of the antibody PP10762 is as set forth in SEQ ID NO: 11.

As another example, the antibody or the antigen binding fragment thereof may comprise a light chain and a heavy chain that are the same as those of the antibody PP10763. The light chain of the antibody PP10763 is as set forth in SEQ ID NO: 20, and the heavy chain of the antibody PP10763 is as set forth in SEQ ID NO: 14.

As another example, the antibody or the antigen binding fragment thereof may comprise a light chain and a heavy chain that are the same as those of the antibody PP10764. The light chain of the antibody PP10764 is as set forth in SEQ ID NO: 23, and the heavy chain of the antibody PP10764 is as set forth in SEQ ID NO: 14.

As another example, the antibody or the antigen binding fragment thereof may comprise a light chain and a heavy chain that are the same as those of the antibody PP10765. The light chain of the antibody PP10765 is as set forth in SEQ ID NO: 26, and the heavy chain of the antibody PP10765 is as set forth in SEQ ID NO: 14.

As another example, the antibody or the antigen binding fragment thereof may comprise a light chain and a heavy chain that are the same as those of the antibody PP10766. The light chain of the antibody PP10766 is as set forth in SEQ ID NO: 20, and the heavy chain of the antibody PP10766 is as set forth in SEQ ID NO: 17.

As another example, the antibody or the antigen binding fragment thereof may comprise a light chain and a heavy chain that are the same as those of the antibody PP10767. The light chain of the antibody PP10767 is as set forth in SEQ ID NO: 23, and the heavy chain of the antibody PP10767 is as set forth in SEQ ID NO: 17.

As another example, the antibody or the antigen binding fragment thereof may comprise a light chain and a heavy chain that are the same as those of the antibody PP10768. The light chain of the antibody PP10768 is as set forth in SEQ ID NO: 26, and the heavy chain of the antibody PP10768 is as set forth in SEQ ID NO: 17.

As another example, the antibody or the antigen binding fragment thereof may comprise a light chain and a heavy chain that are the same as those of the antibody PP10760. The nucleotide encoding the light chain of the antibody PP10760 is as set forth in SEQ ID NO: 22, and the nucleotide encoding the heavy chain of the antibody PP10760 is as set forth in SEQ ID NO: 13.

As another example, the antibody or the antigen binding fragment thereof may comprise a light chain and a heavy chain that are the same as those of the antibody PP10761. The nucleotide encoding the light chain of the antibody PP10761 is as set forth in SEQ ID NO: 25, and the nucleotide encoding the heavy chain of the antibody PP10761 is as set forth in SEQ ID NO: 13.

As another example, the antibody or the antigen binding fragment thereof may comprise a light chain and a heavy chain that are the same as those of the antibody PP10762. The nucleotide encoding the light chain of the antibody PP10762 is as set forth in SEQ ID NO: 28, and the nucleotide encoding the heavy chain of the antibody PP10762 is as set forth in SEQ ID NO: 13.

As another example, the antibody or the antigen binding fragment thereof may comprise a light chain and a heavy chain that are the same as those of the antibody PP10763. The nucleotide encoding the light chain of the antibody PP10763 is as set forth in SEQ ID NO: 22, and the nucleotide encoding the heavy chain of the antibody PP10763 is as set forth in SEQ ID NO: 16.

As another example, the antibody or the antigen binding fragment thereof may comprise a light chain and a heavy chain that are the same as those of the antibody PP10764. The nucleotide encoding the light chain of the antibody PP10764 is as set forth in SEQ ID NO: 25, and the nucleotide encoding the heavy chain of the antibody PP10764 is as set forth in SEQ ID NO: 16.

As another example, the antibody or the antigen binding fragment thereof may comprise a light chain and a heavy chain that are the same as those of the antibody PP10765. The nucleotide encoding the light chain of the antibody PP10765 is as set forth in SEQ ID NO: 28, and the nucleotide encoding the heavy chain of the antibody PP10765 is as set forth in SEQ ID NO: 16.

As another example, the antibody or the antigen binding fragment thereof may comprise a light chain and a heavy chain that are the same as those of the antibody PP10766. The nucleotide encoding the light chain of the antibody PP10766 is as set forth in SEQ ID NO: 22, and the nucleotide encoding the heavy chain of the antibody PP10766 is as set forth in SEQ ID NO: 19.

As another example, the antibody or the antigen binding fragment thereof may comprise a light chain and a heavy chain that are the same as those of the antibody PP10767. The nucleotide encoding the light chain of the antibody PP10767 is as set forth in SEQ ID NO: 25, and the nucleotide encoding the heavy chain of the antibody PP10767 is as set forth in SEQ ID NO: 19.

As another example, the antibody or the antigen binding fragment thereof may comprise a light chain and a heavy chain that are the same as those of the antibody PP10768. The nucleotide encoding the light chain of the antibody PP10768 is as set forth in SEQ ID NO: 28, and the nucleotide encoding the heavy chain of the antibody PP10768 is as set forth in SEQ ID NO: 19.

In some embodiments, the antibody according to the present disclosure is selected from the group consisting of: PP10759, PP10760, PP10761, PP10762, PP10763, PP10764, PP10765, PP10766, PP10767 and PP10768.

In another aspect, the present disclosure provides a fusion protein comprising the antibody or the antigen binding fragment thereof according to the present disclosure. For example, the fusion protein may comprise one or more additional components, such as other pharmaceutically active components. The additional component may be fused to the antibody, or its antigen binding fragment according to the present disclosure directly or indirectly (e.g., via a linker, such as a peptide linker). The fusion protein may still have at least some of the properties of the antibody, or its antigen binding fragment according to the present disclosure.

The antibody or antigen binding fragment may also encompass a homology or a variant thereof having substantially the same function/property thereto. In some cases, the homology or variant may be a polypeptide different from the antibody or antigen binding fragment thereof at least one amino acid. For example, the homology or variant may be a polypeptide different from the antibody or antigen binding fragment thereof by an addition, deletion or substitution of one or more amino acid, such as 1-50, 1-40, 1-30, 1-20, 1-15, 1-14, 1-13, 1-12, 1-11, 1-10, 1-9, 1-8, 1-7, 1-6, 1-5, 1-4, 1-3, or 1-2 amino acids. In some cases, the homology or variant may be a polypeptide having a sequence identity of at least 80% with the antibody or antigen binding fragment thereof. For example, the homology or variant may be a polypeptide having a sequence identity of 80% (e.g., at least 85%, at least 90%, at least 91%, at least 92%, at least 93%, at least 94%, at least 95%, at least 96%, at least 97%, at least 98%, at least 99% or higher) to the antibody or antigen binding fragment thereof.

The term "percent (%) sequence identity," as used in the context of polypeptide sequences identified herein, generally refers to the percentage of amino acid residues or nucleotides in a query sequence that are identical with the amino acid residues or nucleotides of a second, reference polypeptide sequence or a portion thereof, after aligning the sequences and introducing gaps, if necessary, to achieve the maximum percent sequence identity, and not considering any conservative substitutions as part of the sequence identity. Alignment for purposes of determining percent amino acid/nucleotide sequence identity can be achieved in various ways that are within the skill in the art, for instance, using publicly available computer software such as BLAST, BLAST-2, ALIGN, NEEDLE or Megalign (DNASTAR) software. Those skilled in the art can determine appropriate parameters for measuring alignment, including any algorithms needed to achieve maximal alignment over the full length of the sequences being compared. Percent identity may be measured over the length of an entire defined polypeptide/polynucleotide sequence, or may be measured over a shorter length, for example, over the length of a fragment taken from a larger, defined polypeptide/polynucleotide sequence. It is understood that any fragment length supported by the sequences shown herein, in the tables, figures or Sequence Listing, may be used to describe a length over which percentage identity may be measured.

Nucleic Acid, Vector, Cell and the Method of Preparation

In another aspect, the present disclosure provides isolated nucleic acid or molecules, encoding for the antibody or the antigen binding fragment thereof, or the fusion protein.

The isolated nucleic acids may comprise one or more nucleic acid molecules, with each encoding the antibody of the present disclosure or an antigen binding fragment thereof. For example, the isolated nucleic acids may comprise at least two nucleic acid molecules, with one encoding the antibody heavy chain or a fragment thereof, and one encoding the antibody light chain or a fragment thereof. In some cases, the isolated nucleic acids may encode for a fusion protein.

The isolated nucleic acid or isolated nucleic acids may be synthesized using recombinant techniques well known in the art. For example, the isolated nucleic acid or isolated nucleic acids may be synthesized with an automated DNA synthesizer. Standard recombinant DNA and molecular cloning techniques include those described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987). Briefly, the subject nucleic acids may be prepared from genomic DNA fragments, cDNAs, and RNAs, all of which may be extracted directly from a cell or recombinantly produced by various amplification processes including but not limited to PCR and RT-PCR.

Direct chemical synthesis of nucleic acids typically involves sequential addition of 3'-blocked and 5'-blocked nucleotide monomers to the terminal 5'-hydroxyl group of a growing nucleotide polymer chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. See for example, Matteuci et al., *Tet. Lett.* 521:719 (1980); U.S. Pat. No. 4,500,707 to Caruthers et al.; and U.S. Pat. Nos. 5,436,327 and 5,700,637 to Southern et al.

In another aspect, the present disclosure provides a vector or vectors, comprising the isolated nucleic acid molecule or molecules.

The vector may be any linear nucleic acids, plasmids, phagemids, cosmids, RNA vectors, viral vectors and the like. Non-limiting examples of a viral vector may include a retrovirus, an adenovirus and an adeno-associated virus. In some embodiments, the vector is an expression vector, e.g. a phage display vector.

An expression vector may be suitable for use in particular types of host cells and not others. For example, the expression vector can be introduced into the host organism, which is then monitored for viability and expression of any genes/polynucleotides contained in the vector.

The expression vector may also contain one or more selectable marker genes that, upon expression, confer one or more phenotypic traits useful for selecting or otherwise identifying host cells that carry the expression vector. Non-limiting examples of suitable selectable markers for eukaryotic cells include dihydrofolate reductase and neomycin resistance.

The subject vectors can be introduced into a host cell stably or transiently by a variety of established techniques. For example, one method involves a calcium chloride treatment wherein the expression vector is introduced via a calcium precipitate. Other salts, for example calcium phosphate, may also be used following a similar procedure. In addition, electroporation (that is, the application of current to increase the permeability of cells to nucleic acids) may be used. Other examples of transformation methods include microinjection, DEAE dextran mediated transformation, and heat shock in the presence of lithium acetate. Lipid complexes, liposomes, and dendrimers may also be employed to transfect the host cells.

In another aspect, the present disclosure provides a cell (e.g., an isolated cell, such as a host cell), comprising the isolated nucleic acid molecule or molecules of the present disclosure or the vector or vectors of the present disclosure.

The cell may express the antibody, or the antigen binding fragment thereof of the present disclosure, or the fusion protein of the present disclosure. The cell may be a eukaryotic cell or a prokaryotic cell. An appropriate cell may be transformed or transfected with the nucleic acid(s) or vector(s) of the present disclosure and utilized for the expression and/or secretion of the antibody, the antigen binding fragment thereof, or the fusion protein. For example, the cell may be $E.\ coli$ cells, other bacterial host cells, yeast cells, or various higher eukaryotic cells.

In another aspect, the present disclosure provides a method for producing the antibody or the antigen binding fragment thereof, or the fusion protein of the present disclosure, comprising culturing the cell of the present disclosure under conditions enabling expression of the antibody, the antigen binding fragment thereof, or the fusion protein.

The method optionally may further comprise harvesting the antibody or the antigen binding fragment thereof, or the fusion protein of the present disclosure.

Compositions

In another aspect, the present disclosure provides a composition, comprising the antibody or the antigen binding fragment thereof, the fusion protein, the isolated nucleic acid molecule or molecules, the vector or vectors, and/or the cell of the present disclosure, and optionally a pharmaceutically acceptable excipient.

In some embodiments, the composition further comprises an effective amount of an additional therapeutically active component, for example, an additional therapeutically active component for treating a disease or a disorder associated with an inappropriate expression or function of IL-17A. Each of the active components may be present in the pharmaceutical composition in a pharmaceutically active amount. In the composition, the antibody, the fragment thereof of the present application may or may not be associated with the additional active component.

Described below are non-limiting exemplary pharmaceutical compositions and methods for preparing the same. The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. In some embodiments, the pharmaceutical composition may be a liquid pharmaceutical composition.

Pharmaceutical compositions of the disclosure can be presented as discrete dosage forms, with each dosage containing a predetermined amount of an active ingredient as a powder or in granules, a solution, or a suspension in an aqueous or non-aqueous liquid. Such dosage forms can be prepared by any of the methods known to a skilled person, for example, it may include the step of bringing the active ingredient into association with the carrier, which constitutes one or more other ingredients. In general, the compositions are prepared by uniformly and intimately mixing the active ingredient with liquid carriers or finely divided solid carriers or both, and then, if necessary, shaping the product into the desired presentation.

The antibody, the antigen binding fragment thereof, or the fusion protein of the present disclosure can be combined in an intimate admixture with a pharmaceutical carrier according to conventional pharmaceutical compounding techniques. The carrier can take a wide variety of forms depending on the form of preparation desired for administration.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and/or mixtures thereof.

The pharmaceutical compositions of the present disclosure may comprise a therapeutically effective amount of the active agent (e.g., the antibody, the antigen binding fragment thereof, or the fusion protein of the present disclosure). A therapeutically effective amount is an amount of the subject pharmaceutical composition capable of preventing and/or curing (at least partially) a condition or disorder (e.g., an autoimmune diseases) and/or any complications thereof in a subject suffering from or having a risk of developing said condition or disorder. The specific amount/concentration of the active agent comprised may vary according to the method of administration and the need of a patient, and can be determined based on e.g., volume, viscosity, and/or body weight of a patient etc. For example, an appropriate dosage may be about 0.1 mg or 1 mg/kg/day to about 50 mg/kg/day; sometimes, the dosage can be even higher. It shall be understood that these specific doses may be conveniently adjusted by a skilled person in the art (e.g., a doctor or a pharmacist) based on conditions of a specific patient, formulation, and/or disease.

Medical Use and Methods of Treatment

In another aspect, the present disclosure provides a use of the antibody or the antigen binding fragment thereof, the fusion protein, the isolated nucleic acid molecule or molecules, the vector or vectors, and/or the cell of the present disclosure in the manufacture of a medicament for preventing and/or treating a disease or disorder associated with an inappropriate expression or function of IL-17A.

For example, such disease or disorder may be an autoimmune disease, for example, it may comprise psoriasis and/or arthritis (e.g. rheumatoid arthritis (RA)).

In another aspect, the present disclosure provides a method for preventing and/or treating a disease or disorder in a subject in need thereof, comprising administering to said subject an effective amount of the antibody or the antigen binding fragment thereof, the fusion protein, the isolated nucleic acid molecule or molecules, the vector or vectors, and/or the cell of the present disclosure, wherein said disease or disorder is a disease or disorder associated with an inappropriate expression or function of IL-17A. For example, such disease or disorder may be an autoimmune disease, for example, it may comprise psoriasis and/or arthritis (e.g. rheumatoid arthritis (RA)).

In another aspect, the present disclosure provides the antibody or the antigen binding fragment thereof, the fusion protein, the isolated nucleic acid molecule or molecules, the vector or vectors, and/or the cell of the present disclosure, for preventing and/or treating a disease or disorder in a subject in need thereof. For example, such disease or disorder may be an autoimmune disease, for example, it may comprise psoriasis and/or arthritis (e.g. rheumatoid arthritis (RA)).

In another aspect, the present disclosure provides a use of the antibody or the antigen binding fragment thereof, or the fusion protein of the present disclosure in the manufacture of an agent for determining the presence and/or amount of IL-17A in a sample. In some embodiments, said determining is performed in vitro, such as in an in vitro method of sample analysis.

In another aspect, the present disclosure provides a method for determining the presence and/or amount of IL-17A in a sample, comprising: a) contacting the sample with the antibody or the antigen binding fragment thereof, or the fusion protein of the present disclosure; and b) determining the presence and/or amount of said antibody, the antigen binding fragment thereof, or the fusion protein bound to the sample. In some embodiments, such a method is an in vitro method.

In another aspect, the present disclosure provides the antibody or the antigen binding fragment thereof, the fusion protein, the isolated nucleic acid molecule or molecules, the vector or vectors, or the cell of the present disclosure, for determining the presence and/or amount of IL-17A in a sample. In some embodiments, the antibody or the antigen binding fragment thereof, the fusion protein, the isolated nucleic acid molecule or molecules, the vector or vectors, or the cell of the present disclosure may be present in a kit (such as a detection kit), the kit may comprise further materials, such as buffers or an instruction for use.

When the antibody or the antigen binding fragment thereof, the fusion protein, the isolated nucleic acid molecule or molecules, the vector or vectors, or the cell of the present disclosure is used for determining the presence and/or amount of IL-17A in a sample. The sample may generally be any agent/material/mixture suspected or known to comprise or not comprise IL-17A, a fragment thereof. The IL-17A may be a human IL-17A, a monkey IL-17A, and/or a mouse IL-17A. In some embodiments, the sample may be a biological sample, for example, the sample may comprise a body fluid, a tissue or a cell from a subject (e.g., a human or non-human subject). The sample may be purified, or partially purified. In some embodiments, the sample may be from a living environment of a subject, e.g., from the water, the soil or other sources.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

EXAMPLES

The following examples are set forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); i.m., intramuscular(ly); i.p., intraperitoneal(ly); s.c., subcutaneous(ly); and the like.

Example 1 Obtainment of Anti-IL-17A Monoclonal Antibody

A group of BALB/C mice were immunized with recombinant human IL-17A. Spleen cells harvested were fused with SP2/0 myeloma cells. 50% PEG (MW1500) was used as the fusion reagent. The derived hybridoma cells were selected in HAT hybridoma selection medium. Mouse anti-IL-17A monoclonal antibody clone #2P28.3.1 was selected for further study. After sequencing, the amino acid sequence of the VH and VL of 2P28.3.1 (i.e. VH6664 and VL6664, respectively) was obtained, as set forth in SEQ ID NO. 7 and SEQ ID NO. 8, respectively.

A chimeric antibody PP10759 was then obtained by fusing the VH region of 2P28.3.1 to the human IgG4 constant region, and fusing the VL region of 2P28.3.1 to the human Igκ constant region. The amino acid sequence of the heavy chain of PP10759 (i.e. PP10759H and heavy chain 6664) is as set forth in SEQ ID NO: 9, and the amino acid sequence of the light chain of PP10759 (i.e. PP10759L and light chain 6664) is as set forth in SEQ ID NO: 10.

Example 2 Humanization of Anti-IL-17A Monoclonal Antibodies

Mouse sequences in an antibody may cause undesired immunogenicity in humans. To maximize the amount of human sequence in the antibodies while retaining the original antibody specificity, the humanization of the parental antibody was performed by using in silico analyses, for matching interface position, similarly classed CDR canonical positions, and removing presence of N-glycosylation sites and creating multiple hybrid sequences that fuse select parts of the parental antibody sequence with the human framework sequences.

Figure 1:
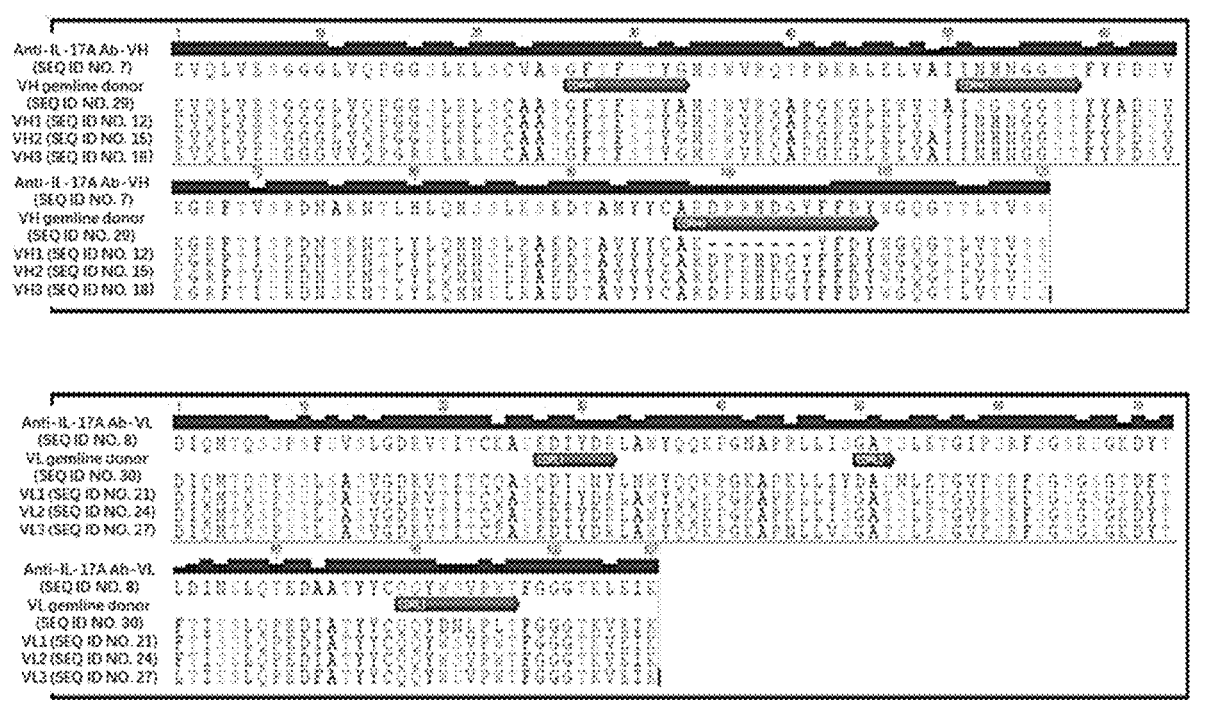

From this analysis, three humanized light chains and three humanized heavy chains were obtained. The variable regions of the three humanized heavy chains are referred to as VH1-3 respectively (i.e. VH6665-VH6667), and the variable regions of the three humanized light chains are referred to as VL 1-3 respectively (i.e. VL6665-VL6667), as shown in FIG. 1. The amino acid sequences of VH6665-VH6667 are as set forth in SEQ ID NO. 12, SEQ ID NO. 15 and SEQ ID NO. 18, respectively; and the amino acid sequences of VL6665-VL6667 are as set forth in SEQ ID NO. 21, SEQ ID NO. 24 and SEQ ID NO. 27 respectively.

After combining the three humanized light chains with the three humanized heavy chains, 9 humanized antibodies were obtained by replacing the VH and VL of PP10759 with respective humanized VH and VL sequences (i.e. VH6665-VH6667 and VL6665-VL6667). The 9 humanized antibodies thus obtained are named as PP10760-PP10768.

The sequences of PP10759-PP10768 were artificially synthesized and sequenced for accuracy, and were recombinantly cloned into the vector pCDNA3.1 respectively. The vectors were transfected into HEK293 cells for transient expression, then the cells were cultured under proper conditions for the expression of the antibodies. The 9 humanized antibodies PP10760-PP10768 and the chimeric antibody PP10759 were harvested from the cells, and then purified by ProteinA purification.

The amino acid sequences of the antibodies are shown in Table 1:

TABLE 1

| Antibody | VH | SEQ ID No. | VL | SEQ ID No. |
|---|---|---|---|---|
| PP10759 | VH6664 | SEQ ID No. 7 | VL6664 | SEQ ID No. 8 |
| PP10760 | VH6665 | SEQ ID No. 12 | VL6665 | SEQ ID No. 21 |
| PP10761 | VH6665 | SEQ ID No. 12 | VL6666 | SEQ ID No. 24 |
| PP10762 | VH6665 | SEQ ID No. 12 | VL6667 | SEQ ID No. 27 |
| PP10763 | VH6666 | SEQ ID No. 15 | VL6665 | SEQ ID No. 21 |
| PP10764 | VH6666 | SEQ ID No. 15 | VL6666 | SEQ ID No. 24 |
| PP10765 | VH6666 | SEQ ID No. 15 | VL6667 | SEQ ID No. 27 |
| PP10766 | VH6667 | SEQ ID No. 18 | VL6665 | SEQ ID No. 21 |
| PP10767 | VH6667 | SEQ ID No. 18 | VL6666 | SEQ ID No. 24 |
| PP10768 | VH6667 | SEQ ID No. 18 | VL6667 | SEQ ID No. 27 |

Example 3 Assessment of the Humanness of Monoclonal Antibodies

The humanness of the monoclonal antibodies after their humanization was evaluated by the calculation of their humanness scores. The humanness scores for the parental and the 9 humanized antibodies obtained in Example 2 are shown in Table 2.1. and 2.2.

According to the method of Gao, S. H., Huang, K., Tu, H., and Adler, A. S. 2013. Monoclonal antibody humanness score and its applications. *BMC Biotechnology*, 13:55, for heavy chains a score of 79 or above is indicative of looking human-like; for kappa light chains a score of 86 or above is indicative of looking human-like. As the results of Table 2.1. and 2.2 indicate, the 9 humanized antibodies shall be considered human-like.

TABLE 2.1

| VH | Full-length (Framework + CDR) Cutoff = 79 | Framework Only Cutoff = 84 |
|---|---|---|
| VH6664 | 74.5 | 77.4 |
| VH6665 | 86.4 | 92.2 |
| VH6666 | 84.7 | 89.9 |
| VH6667 | 84.0 | 91.9 |

TABLE 2.2

| VL | Full-length (Framework + CDR) Cutoff = 86 | Framework Only Cutoff = 90 |
|---|---|---|
| VL6664 | 71.5 | 78.3 |
| VL6665 | 85.1 | 94.5 |
| VL6666 | 84.4 | 93.3 |
| VL6667 | 83.0 | 91.6 |

Example 4 Binding Activities of the Antibodies

To evaluate the binding affinity and specificity of the antibodies obtained in Example 1 and 2, multiple binding assays were performed.

4.1 Affinity Measurement by Octet

Figure 2B:
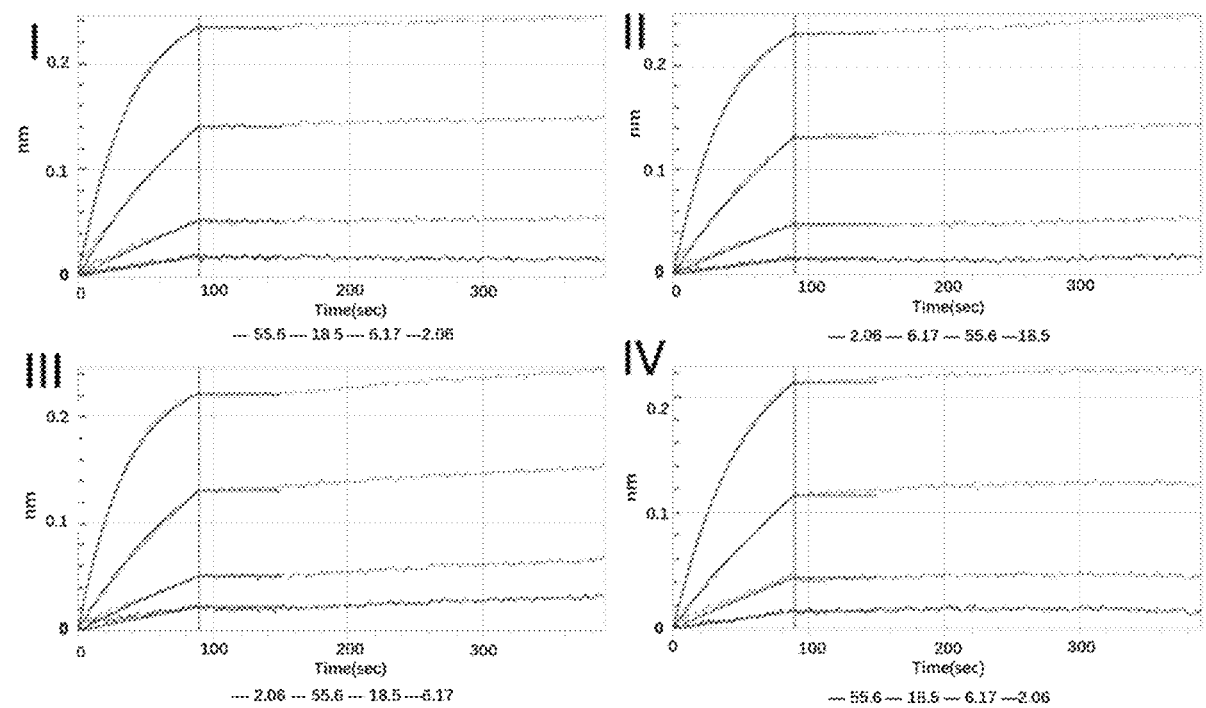
Figure 2C:
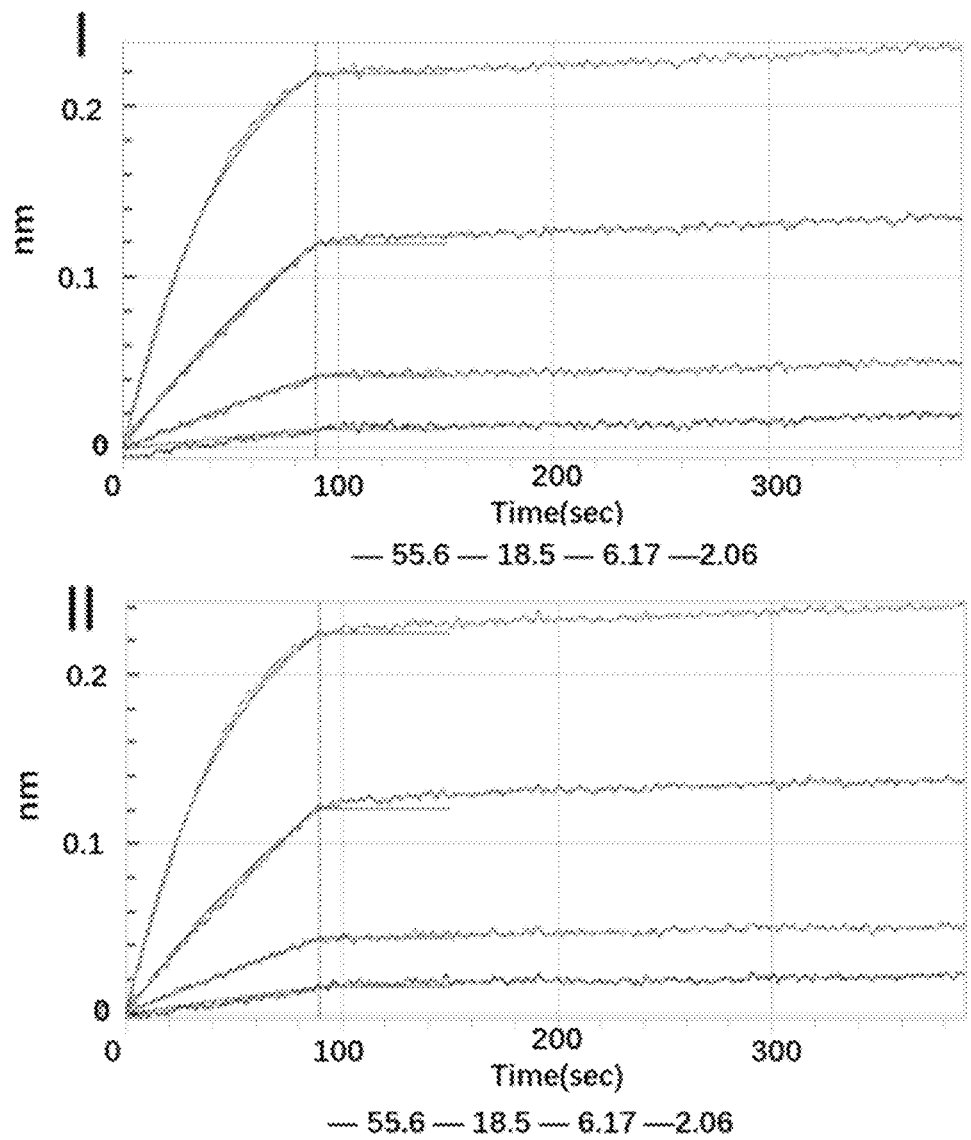

Using the Octet method (Fortebio Octet®), the chimeric parental antibody and the 9 humanized antibodies (i.e. PP10759-PP10768) were evaluated with Octet Red96 at 25° C. These antibodies were captured on anti-Human Fc (AHC) biosensors at a concentration of 10 μg/mL. Loaded biosensors were then dipped into a dilution of antigen (human IL-17A (R&D Systems), 500 nM start, 1:3 down, 7 points). Kinetic constants were calculated using a monovalent (1:1) model. The results are shown in Table 3 and in FIG. 2A-2C. In FIG. 2A, Figure I, II, III and IV show the results of PP10759, PP10760, PP10761 and PP10762, respectively. In FIG. 2B, Figure I, II, III and IV show the results of PP10763, PP10764, PP10765 and PP10766, respectively. In FIG. 2B, Figure I and II show the results of PP10767 and PP10768, respectively. It can be seen that the antibodies (i.e. PP10759-PP10768) bind to IL-17A with high affinity. And this affinity is comparable or higher than the $K_D$ of Secukinuma (which is $3.7 \times 10^{-10}$M). Secukinuma is a human IgG1 Kmonoclonal antibody that binds to IL-17A made by Novartis.

TABLE 3

| Antibody Name | $K_D$ (M) | Kon (1/Ms) | Kdis (1/s) | Full X * 2 | Full R * 2 |
|---|---|---|---|---|---|
| PP10759 | 1.1E−09 | 4.8E+05 | 5.3E−04 | 0.0040 | 0.9983 |
| PP10760 | 3.10E−10 | 4.9E+05 | 1.5E−04 | 0.0049 | 0.9984 |
| PP10761 | <1.0E−12 | 4.0E+05 | <1.0E−07 | 0.0104 | 0.9968 |
| PP10762 | <1.0E−12 | 4.4E+05 | <1.0E−07 | 0.0070 | 0.998 |
| PP10763 | 3.6E−10 | 4.6E+05 | 1.6E−04 | 0.0042 | 0.9989 |
| PP10764 | <1.0E−12 | 4.5E+05 | <1.0E−07 | 0.0040 | 0.9989 |
| PP10765 | 1.3E−10 | 5.0E+05 | 6.6E−05 | 0.0049 | 0.9985 |
| PP10766 | <1.0E−12 | 3.5E+05 | <1.0E−07 | 0.0033 | 0.9989 |
| PP10767 | <1.0E−12 | 3.6E+05 | <1.0E−07 | 0.0038 | 0.9989 |
| PP10768 | <1.0E−12 | 3.7E+05 | <1.0E−07 | 0.0061 | 0.9983 |

4.2 Binding of the Humanized Antibodies to Human IL-17A (ELISA)

Figure 3:
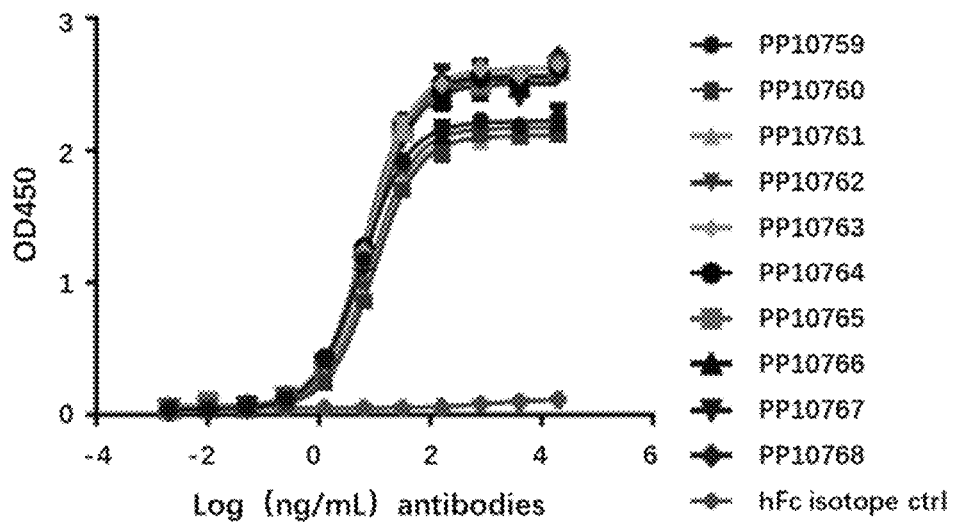
FIG. 3 illustrates the binding affinity of the antibodies of the present disclosure, as measured in ELISA.

ELISA plates were coated with 1 μg/mL IL-17 antigen (human IL17A) (R&D Systems) and incubated at 4° C. in the dark overnight. Then it was washed once with 10 mM, pH 7.4 PBS/Tween (0.05%), blocked with PBST containing 2% BSA for 1 hour and incubated at room temperature for 1 h. The antibodies PP10759-PP10768 were diluted in 5-fold increments for a total of eleven data points and were added to the ELISA wells and incubated at room temperature for 1 hour. The plate was washed with PBS for three times, and then incubated with HRP conjugated goat anti-human IgG antibody for 1 hour. The plate was washed three times with PBS. TMB, the HRP substrate, was added to each well for color development for 5 minutes at room temperature. Equal amount of 0.1N HCl stop solution was added to each well to terminate the reaction. Raw $OD_{450}$ data was collected by POLARstar Omega (BMG Labtech). Besides, hFc isotype was regarded as control. The results are shown in Table 4 and FIG. 3. It can be seen that the antibodies (i.e. PP10759-PP10768) bind to human IL-17A with high affinity.

TABLE 4

| Antibody Name | EC50 (ng/ml) |
|---|---|
| PP10759 | 5.83 |
| PP10760 | 9.44 |
| PP10761 | 8.72 |
| PP10762 | 8.26 |
| PP10763 | 7.28 |
| PP10764 | 6.61 |
| PP10765 | 7.61 |
| PP10766 | 7.35 |
| PP10767 | 7.71 |
| PP10768 | 7.67 |

4.3 Binding Specificity of the Antibodies to Monkey IL-17A

It is often desired that a therapeutic antibody also binds to antigens of a model animal, to facilitate pre-clinical study. Therefore, the ability of the antibodies PP10759-PP10768 to bind mouse IL-17A or cynomolgus monkey IL17A was evaluated. The evaluation method was the same as that described in 4.2 except that IL-17 antigen (human IL17A) was replaced by monkey IL-17A or mouse IL-17A.

Figure 4:
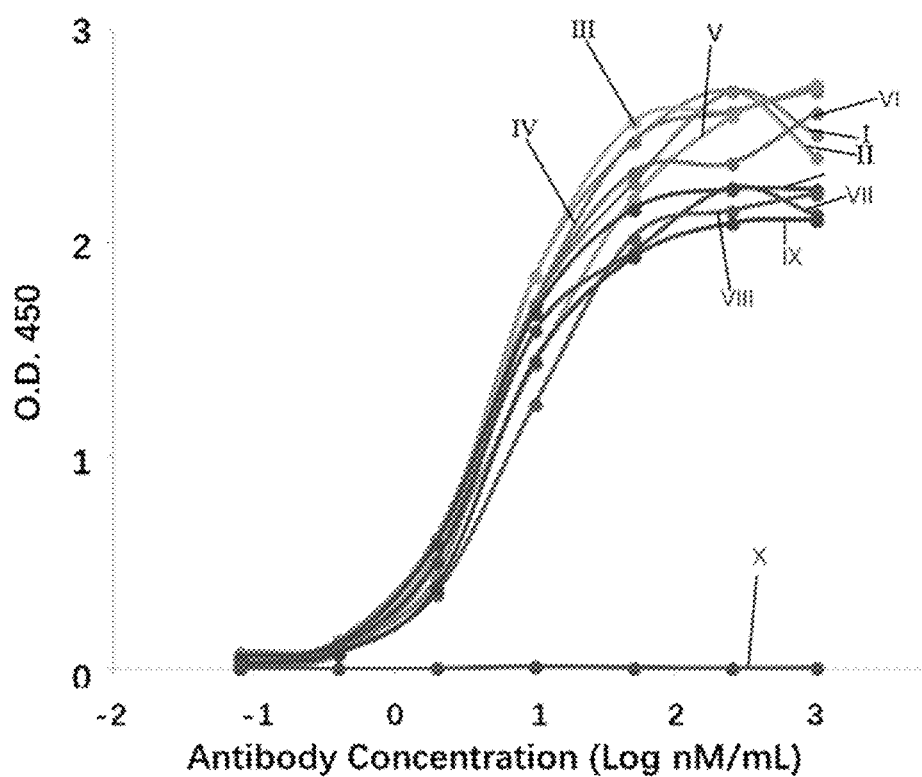
FIG. 4 illustrates the binding affinity of the antibodies of the present disclosure, as measured in ELISA.

The ELISA data of monkey IL-17A and mouse IL-17A are shown in FIG. 4. In FIG. 4, I, II, III, IV, V, VI, VII, VIII and IX show the affinity of antibodies PP10759, PP10760, PP10761, PP10762, PP10763, PP10764, PP10765, PP10766, PP10767 and PP10768 to cynomolgus monkey IL17A, respectively. And X shows the affinity of antibodies PP10759-PP10768 to mouse IL-17A. It can be seen that the antibodies PP10759-PP10768 bind to cynomolgus monkey IL17A with high affinity, but they do not bind to mouse IL-17A.

Example 5 the Ability of the Antibodies to Block an Interaction Between Human IL-17A and Human IL-17R Recombinant human IL-17RA or recombinant human IL-17RC (1p g/ml) were coated on the plate, overnight at 4° C. in the dark and then blocked with 2% BSA for 1 hour at room temperature to reduce non-specific binding. The antibodies PP10759-PP10768 (1 µg/ml) pre-mixed with human IL-17A (0.1p g/ml final concentration) were added to the ELISA wells for 1 hour at room temperature. The plate was washed with PBS for three times, and then incubated with anti-IL17A polyclonal Ab-biotin (R&D Systems) for 1 hour followed by SAV-HRP. The plate was washed for three times with PBS. TMB, the HRP substrate, was added to each well for color development for 5 minutes at room temperature. Equal amount of 0.1N HCl stop solution was added to each well to terminate the reaction. Raw $OD_{450}$ data was collected by POLARstar Omega from BMG Labtech.

The results are shown in Table 5. It can be seen that the antibodies PP10759-PP10768 can effectively block the interaction between IL-17A and IL-17RA as well as IL-17A and IL-17RC.

TABLE 5

| Blocking antibodies | IL-17A/ IL-17RA $OD_{450}$ | Blocking % | IL-17A/ IL-17RC $OD_{450}$ | Blocking % |
|---|---|---|---|---|
| PP10759 | 0.0872 | 99.54 | 0.0888 | 95.23 |
| PP10760 | 0.109 | 97.8 | 0.0762 | 98.04 |
| PP10761 | 0.0851 | 99.66 | 0.0688 | 99.81 |
| PP10762 | 0.0846 | 99.6 | 0.0701 | 99.5 |
| PP10763 | 0.1045 | 90.94 | 0.0721 | 98.92 |
| PP10764 | 0.1263 | 96.49 | 0.0725 | 98.92 |
| PP10765 | 0.2133 | 89.86 | 0.088 | 95.23 |
| PP10766 | 0.1475 | 94.88 | 0.0682 | 99.95 |
| PP10767 | 0.1055 | 98.07 | 0.0684 | 99.9 |
| PP10768 | 0.0869 | 99.49 | 0.0685 | 99.88 |
| Normal human IgG | 1.3934 | 0 | 0.4873 | 0 |
| (—) human IL17A | 0.0798 | 0 | 0.068 | 0 |

Example 6 Humanized IL-17A Antibodies Neutralized Human IL-17A In Vivo

The study was performed in C57BL/6 mice. Experimental animals were received a subcutaneous (SC) injection of human IL-17A, and humanized IL-17A antibodies were administered intravenously to mice in multiple doses 1 hour prior to the injection of human IL-17A. Blood samples were collected at 2 hours post-IL-17A administration in each animal, and CXCL1 (KC) chemokine level in the plasma was determined by ELISA. Human IgG4 was used as an isotype control antibody. The pairwise comparison of KC chemokine levels between treatments was performed using the one-way analysis of variance.

Figure 5:
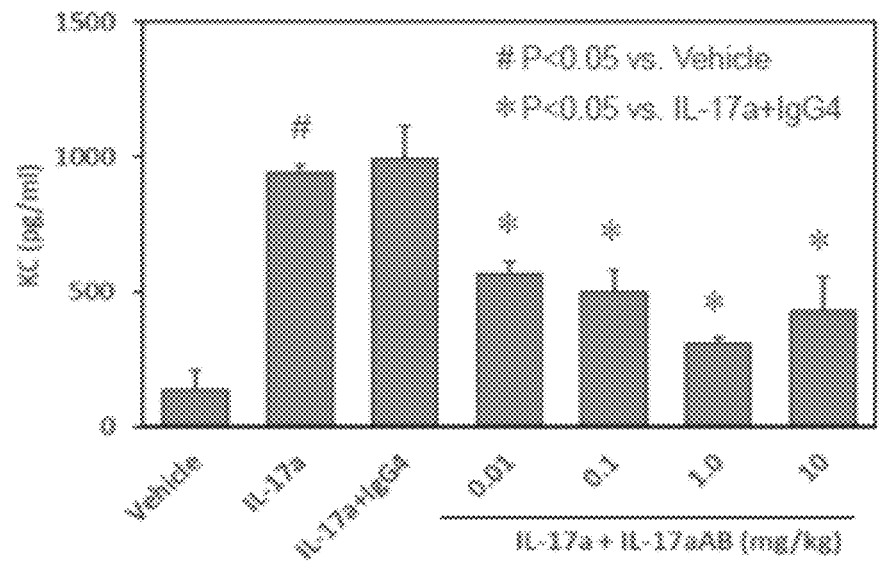
FIG. 5 illustrates that the antibodies neutralize human IL-17a in vivo.

The results are shown in FIG. 5. It can be seen that the administration of human IL-17A to C57BL/6 mice increases plasma KC levels in mouse. Compared to the isotype control treatment, humanized IL-17A antibodies were able to significantly decrease human IL-17A-induced KC secretion in the plasma. These results demonstrate that humanized IL-17A antibodies was able to effectively neutralize human IL-17A in vivo.

Example 7 Humanized IL-17A Antibodies Relieved Arthritis Symptoms in Monkeys

The study was performed in adult cynomolgus monkeys (male and female, 2.5-4.5 kg) with collagen-induced arthritis (CIA). Briefly, arthritis was induced by Bovine collagen type II. Bovine collagen type II solution (4 mg/mL) dissolved in 0.1 M acetic acid and emulsified in an equal volume of complete Freund's adjuvant (CFA). Under anesthesia, each monkey was intracutaneously immunized with 2 mL of the emulsion on the back. These animals received a second immunization with Bovine collagen type II 3 weeks later in the same manner. Then humanized IL-17A antibodies were subcutaneously administrated weekly. Clinical arthritis index, systematic measurement of disease symptoms including joint swelling, erythema, weight loss and impairment of movement, were weekly assessed in all experimental CIA animals.

Figure 6:
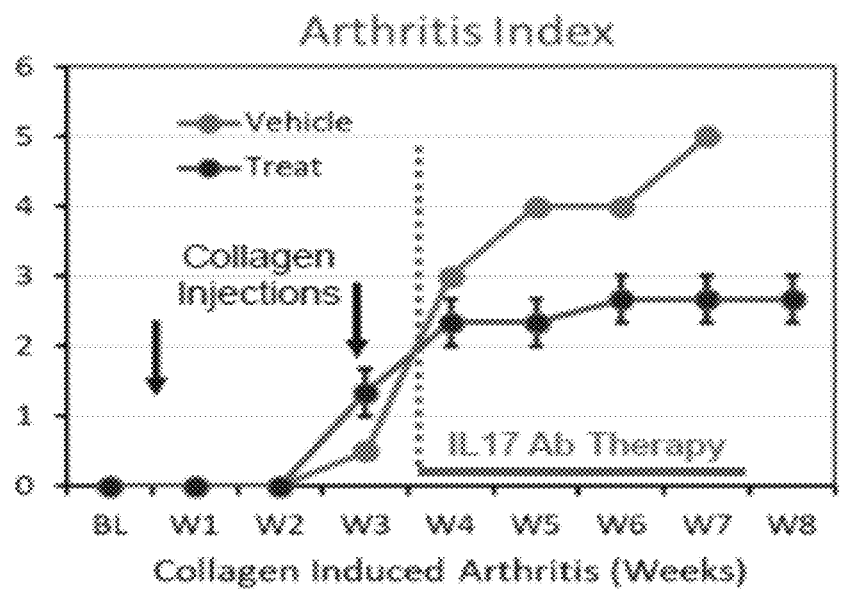
FIG. 6 illustrates that the antibodies relieve arthritis symptoms in monkeys.

The results demonstrated that after the second immunization with collagen, all animals developed clinical arthritis symptoms, including joint swelling, erythema, weight loss and impairment of movement, and their arthritis index were higher (FIG. 6). Compared with control animals, the arthritis index was much lower in animals after the treatment with humanized IL-17A antibodies. These results indicated that humanized IL-17A antibodies was effective in therapy to relieve arthritic symptoms in monkeys with arthritis.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. An antibody or an antigen binding fragment thereof comprising light chain CDR1-3 and heavy chain CDR1-3, wherein the light chain CDR1-3 comprises the amino acid sequence as set forth in SEQ ID NO: 4-6, respectively, and the heavy chain CDR1-3 comprises the amino acid sequence as set forth in SEQ ID NO: 1-3, respectively, and the antibody or an antigen binding fragment thereof which binds to IL-17A and exhibits at least one of the following properties:

a) binds to IL-17A with a $K_D$ of $2 \times 10^{-9}$ M or less, as measured by bio-layer interferometry;
b) specifically binds to IL-17A, and does not substantially bind to IL-17B, IL-17C, IL-17D, IL-17E, or IL-17F;
c) blocks an interaction between IL-17A and IL-17R;
d) neutralizes IL-17A in vivo;
e) is capable of treating an autoimmune disease or disorder.

2. The antibody or the antigen binding fragment thereof according to claim 1, wherein said antibody comprise a light chain or a fragment thereof, wherein said light chain or a fragment thereof comprises a light chain variable region, and said light chain variable region comprises the amino acid sequence as set forth in SEQ ID NO: 8, SEQ ID NO: 21, SEQ ID NO: 24 and SEQ ID NO: 27.

3. The antibody or the antigen binding fragment thereof according to claim 1, wherein said antibody comprise a light chain or a fragment thereof, wherein said light chain or a fragment thereof comprises the amino acid sequence selected from SEQ ID NO: 10, SEQ ID NO: 20, SEQ ID NO: 23 and SEQ ID NO: 26.

4. The antibody or the antigen binding fragment thereof according to claim 1, wherein said antibody comprise a heavy chain or a fragment thereof, wherein said heavy chain or a fragment thereof comprises a heavy chain variable region, and said heavy chain variable region comprises the amino acid sequence selected from SEQ ID NO: 7, SEQ ID NO: 12, SEQ ID NO: 15 and SEQ ID NO: 18.

5. The antibody or the antigen binding fragment thereof according to claim 1, wherein said antibody comprise a heavy chain or a fragment thereof, wherein said heavy chain or a fragment thereof comprises a heavy chain constant region, and said heavy chain constant region comprises a human IgG constant region.

6. The antibody or the antigen binding fragment thereof according to claim 5, wherein said human IgG constant region comprises an IgG4 constant region.

7. The antibody or the antigen binding fragment thereof according to claim 1, wherein said antibody comprise a heavy chain or a fragment thereof, wherein said heavy chain or a fragment thereof comprises the amino acid sequence selected from SEQ ID NO: 9, SEQ ID NO: 11, SEQ ID NO: 14 and SEQ ID NO: 17.

8. The antibody or the antigen binding fragment thereof according to claim 1, wherein said IL-17A is selected from the group consisting of: a human IL-17A and a monkey IL-17A.

9. The antibody or the antigen binding fragment thereof according to claim 1, which specifically binds to human IL-17A and cynomolgus monkey IL-17A.

10. The antibody or the antigen binding fragment thereof according to claim 1, comprising:
   a) a light chain variable region comprising the amino acid sequence as set forth in SEQ ID NO: 8, and a heavy chain variable region comprising the amino acid sequence as set forth in SEQ ID NO: 7;
   b) a light chain variable region comprising the amino acid sequence as set forth in SEQ ID NO: 21, and a heavy chain variable region comprising the amino acid sequence as set forth in SEQ ID NO: 12;
   c) a light chain variable region comprising the amino acid sequence as set forth in SEQ ID NO: 24, and a heavy chain variable region comprising the amino acid sequence as set forth in SEQ ID NO: 12;
   d) a light chain variable region comprising the amino acid sequence as set forth in SEQ ID NO: 27, and a heavy chain variable region comprising the amino acid sequence as set forth in SEQ ID NO: 12;
   e) a light chain variable region comprising the amino acid sequence as set forth in SEQ ID NO: 21, and a heavy chain variable region comprising the amino acid sequence as set forth in SEQ ID NO: 15;
   f) a light chain variable region comprising the amino acid sequence as set forth in SEQ ID NO: 24, and a heavy chain variable region comprising the amino acid sequence as set forth in SEQ ID NO: 15;
   g) a light chain variable region comprising the amino acid sequence as set forth in SEQ ID NO: 27, and a heavy chain variable region comprising the amino acid sequence as set forth in SEQ ID NO: 15;
   h) a light chain variable region comprising the amino acid sequence as set forth in SEQ ID NO: 21, and a heavy chain variable region comprising the amino acid sequence as set forth in SEQ ID NO: 18;
   i) a light chain variable region comprising the amino acid sequence as set forth in SEQ ID NO: 24, and a heavy chain variable region comprising the amino acid sequence as set forth in SEQ ID NO: 18; or,
   j) a light chain variable region comprising the amino acid sequence as set forth in SEQ ID NO: 27, and a heavy chain variable region comprising the amino acid sequence as set forth in SEQ ID NO: 18.

11. A composition comprising the antibody or the antigen binding fragment thereof according to claim 1.

12. The composition of claim 11 and a pharmaceutically acceptable excipient.

13. A method for treating a disease or disorder in a subject in need thereof, comprising administering to said subject an effective amount of the antibody or the antigen binding fragment thereof according to claim 1, wherein said disease or disorder is a disease or disorder associated with an increased expression or function of IL-17A.

14. The method according to claim 13, wherein said disease or disorder comprises psoriasis and/or rheumatoid arthritis (RA).

* * * * *